US009625368B2

(12) United States Patent
Goodwin et al.

(10) Patent No.: US 9,625,368 B2
(45) Date of Patent: Apr. 18, 2017

(54) APPARATUS, OPTICAL ASSEMBLY, METHOD FOR INSPECTION OR MEASUREMENT OF AN OBJECT AND METHOD FOR MANUFACTURING A STRUCTURE

(75) Inventors: Eric Peter Goodwin, Tucson, AZ (US); David Michael Williamson, Tucson, AZ (US); Daniel Gene Smith, Tucson, AZ (US); Michel Pharand, Los Gatos, CA (US); Alexander Cooper, Belmont, CA (US); Alec Robertson, Palo Alto, CA (US); Brian L. Stamper, Tucson, AZ (US)

(73) Assignee: Nikon Corporation, Tokyo (JP)

( * ) Notice: Subject to any disclaimer, the term of this patent is extended or adjusted under 35 U.S.C. 154(b) by 944 days.

(21) Appl. No.: 13/281,393

(22) Filed: Oct. 25, 2011

(65) Prior Publication Data
US 2012/0188557 A1  Jul. 26, 2012

Related U.S. Application Data

(60) Provisional application No. 61/455,768, filed on Oct. 25, 2010.

(51) Int. Cl.
*G01C 3/08* (2006.01)
*G01N 21/01* (2006.01)
(Continued)

(52) U.S. Cl.
CPC ........ *G01N 21/01* (2013.01); *G01B 11/026* (2013.01); *G01S 7/4814* (2013.01); *G01S 7/4817* (2013.01);
(Continued)

(58) Field of Classification Search
CPC ...... G01B 9/02; G01B 11/14; G01B 11/2441; G01S 17/36; G01S 7/491
(Continued)

(56) References Cited

U.S. PATENT DOCUMENTS 3,844,660 A * 10/1974 Hunter .......................... 356/508
4,466,286 A *  8/1984 Berbee et al. ................. 73/629
(Continued)

FOREIGN PATENT DOCUMENTS

EP      0 283 222     9/1988
EP      1058142       12/2000
(Continued)

OTHER PUBLICATIONS

Extended European Search Report from European Application No. EP 11 83 8550, dated Jun. 2, 2014, 7 pages.
(Continued)

*Primary Examiner* — Luke Ratcliffe
*Assistant Examiner* — Samantha K Abraham
(74) *Attorney, Agent, or Firm* — Klarquist Sparkman, LLP

(57) ABSTRACT

An optical assembly for a system for inspecting or measuring of an object is provided that is configured to move as a unit with a system, as the system is pointed at a target, and eliminates the need for a large scanning (pointing) mirror that is moveable relative to other parts of the system. The optical assembly comprises catadioptric optics configured to fold the optical path of the pointing beam and measurement beam that are being directed through the outlet of the system, to compress the size of the optical assembly.

27 Claims, 21 Drawing Sheets

(51) Int. Cl.
*G01B 11/02* (2006.01)
*G01S 7/481* (2006.01)
*G01N 21/17* (2006.01)

(52) U.S. Cl.
CPC .... *G01N 2021/1793* (2013.01); *G01S 7/4818* (2013.01)

(58) Field of Classification Search
USPC .................................................. 356/4.01, 496
See application file for complete search history.

(56) References Cited

U.S. PATENT DOCUMENTS

| | | | |
|---|---|---|---|
| 4,652,130 A * | 3/1987 | Tank | 356/455 |
| 4,733,609 A | 3/1988 | Goodwin et al. | |
| 4,824,251 A | 4/1989 | Slotwinski et al. | |
| 4,830,486 A | 5/1989 | Goodwin | |
| 4,969,736 A | 11/1990 | Slotwinski | |
| 5,056,918 A * | 10/1991 | Bott | G01N 15/0211 356/336 |
| 5,073,016 A * | 12/1991 | Burke | 359/727 |
| 5,114,226 A | 5/1992 | Goodwin et al. | |
| 5,196,713 A | 3/1993 | Marshall | |
| 5,438,449 A * | 8/1995 | Chabot | G01C 21/00 359/211.1 |
| 6,285,476 B1 | 9/2001 | Carlson | |
| 6,556,338 B2 | 4/2003 | Han | |
| 6,747,733 B2 | 6/2004 | Shirai et al. | |
| 6,772,630 B2 | 8/2004 | Araya | |
| 7,106,452 B2 | 9/2006 | Ouchi | |
| 7,139,446 B2 | 11/2006 | Slotwinski | |
| 7,379,191 B2 | 5/2008 | Brooks | |
| 7,388,674 B2 | 6/2008 | Yanaka et al. | |
| 7,796,272 B2 | 9/2010 | Holzapfel | |
| 7,925,134 B2 | 4/2011 | Slotwinski et al. | |
| 7,933,055 B2 | 4/2011 | Jensen et al. | |
| 8,699,007 B2 * | 4/2014 | Becker et al. | 356/4.01 |
| 2002/0036971 A1 * | 3/2002 | Motegi et al. | 369/112.19 |
| 2007/0058154 A1 | 3/2007 | Reichert et al. | |
| 2007/0242258 A1 | 10/2007 | Hinderling et al. | |
| 2008/0205246 A1 | 8/2008 | Shimano et al. | |
| 2008/0278715 A1 | 11/2008 | Swenson et al. | |
| 2008/0285058 A1 | 11/2008 | Holzapfel | |
| 2009/0034061 A1 | 2/2009 | Dodoc | |
| 2009/0039261 A1 * | 2/2009 | Toyoda et al. | 250/310 |
| 2009/0131800 A1 * | 5/2009 | Liang | 600/476 |
| 2009/0303495 A1 * | 12/2009 | Courteville | 356/625 |
| 2010/0134880 A1 * | 6/2010 | Mann | 359/364 |
| 2013/0099957 A1 | 4/2013 | Goodwin et al. | |
| 2013/0194563 A1 | 8/2013 | Goodwin et al. | |

FOREIGN PATENT DOCUMENTS

| | | |
|---|---|---|
| EP | 1058142 B1 | 2/2004 |
| JP | S57-16908 | 6/1980 |
| JP | S61-284606 | 12/1986 |
| JP | S62-121303 | 6/1987 |
| JP | H02-141691 | 5/1990 |
| JP | 2664399 | 10/1997 |
| JP | H9-304532 | 11/1997 |
| JP | H10-293204 | 4/1998 |
| JP | H10-213661 | 8/1998 |
| JP | 1998-293204 | 11/1998 |
| JP | 2002-071515 | 3/2002 |
| JP | 2002-340554 | 11/2002 |
| JP | 2002340554 A * | 11/2002 |
| JP | 2003-139534 | 5/2003 |
| JP | 2003-172612 | 6/2003 |
| JP | 2003-215151 | 7/2003 |
| JP | 2006-194846 | 7/2006 |
| JP | 2007-057522 | 3/2007 |
| JP | 2007057522 B2 * | 3/2007 |
| JP | 2007-538277 | 12/2007 |
| JP | 2008-020332 | 1/2008 |
| JP | 2008020332 A * | 1/2008 |
| JP | 2008-216238 | 9/2008 |
| JP | 2010-501069 | 1/2010 |
| JP | 2010501069 A * | 1/2010 |

OTHER PUBLICATIONS

Japanese Office Action for related Application No. JP 2013-536753, mailed Apr. 1, 2014, 10 pages.
Korean Office Action for related Application No. 10-2013-7013385, mailed Jun. 18, 2014, 17 pages.
International Search Report and Written Opinion from International Application No. PCT/US2011/057758 dated Feb. 16, 2012, 14 pp.
Office Action for related U.S. Appl. No. 13/281,397, 8 pages, mailed on Aug. 22, 2013.
Notice of Allowance for related U.S. Appl. No. 13/281,397, 8 pages, mailed on Dec. 30, 2013.
Notice of Preliminary Rejection from Korean Patent Application No. 10-2013-7013385, dated Jan. 30, 2015, 8 pages (English translation).
Office Action from Canadian Patent Application No. 2,815,094, dated Sep. 11, 2014, 3 pages.
Notification of Reason for Refusal from related Japanese Patent Application No. 2013-536753, dated Dec. 16, 2014, 7 pages (with English translation).
Notification of Reason for Refusal from related Japanese Patent Application No. 2013-536753, dated Mar. 10, 2015, 9 pages. (with English translation).
Office action from U.S. Appl. No. 13/828,221, dated Jan. 9, 2015, 12 pages.
Decision to Dismiss Amendment from related Japanese Patent Application No. 2013-536753, dated Jun. 23, 2015, 8 pages (with English translation).
Decision of Refusal from related Japanese Patent Application No. 2013-536753, dated Jun. 23, 2015, 3 pages (with English translation).
Office Action from Canadian Patent Application No. 2,815,094, dated Aug. 14, 2015, 4 pages.
Notice of Grounds for Rejection from Korean Patent Application No. 2013-7013385, dated Oct. 30, 2015, 16 pages (with English translation).

* cited by examiner

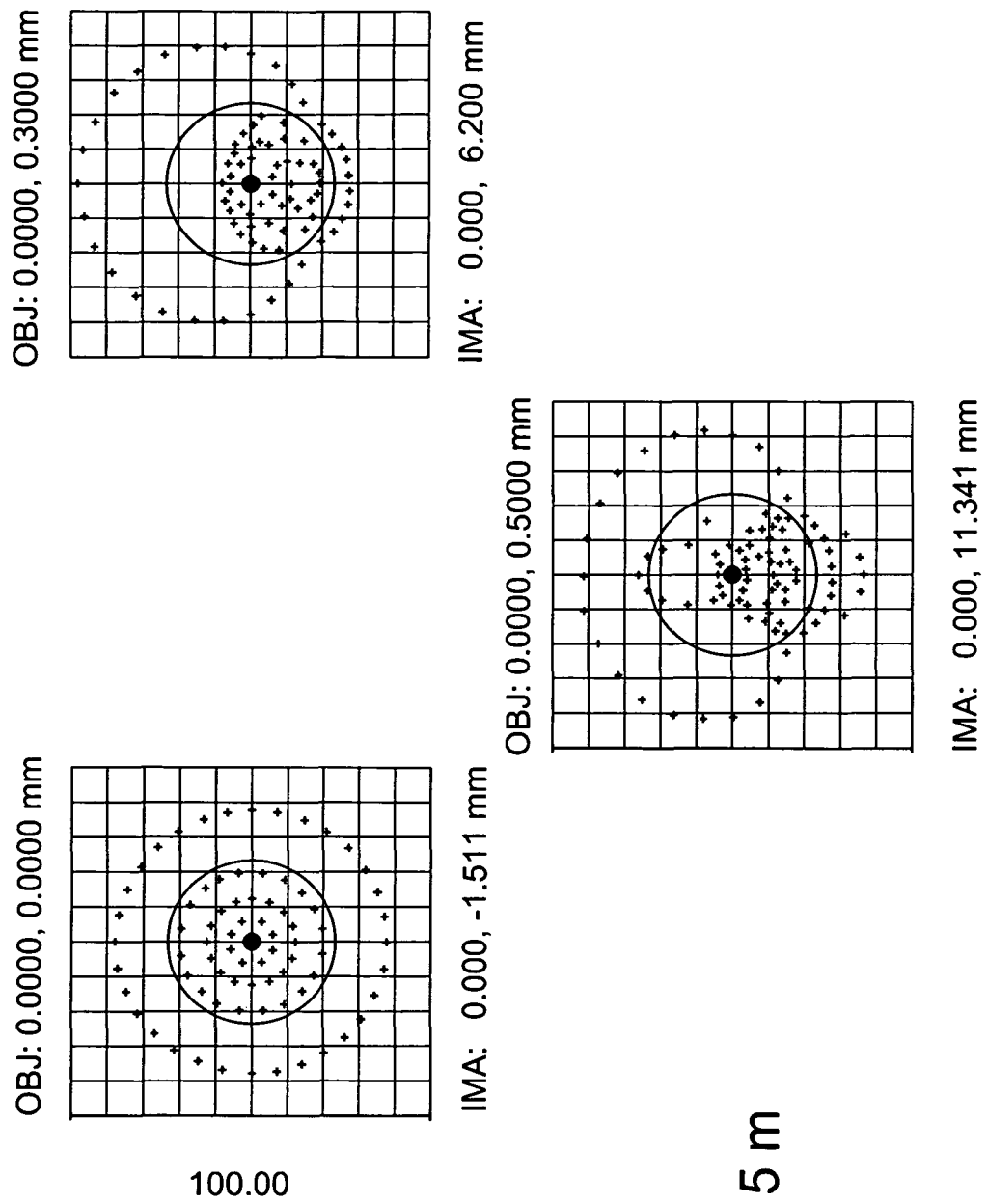

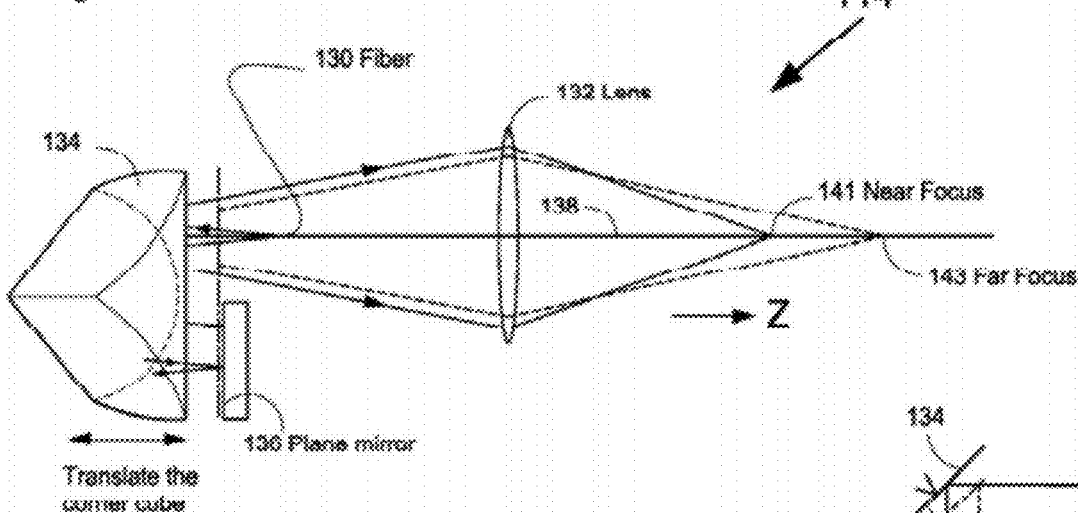
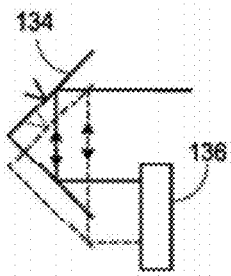

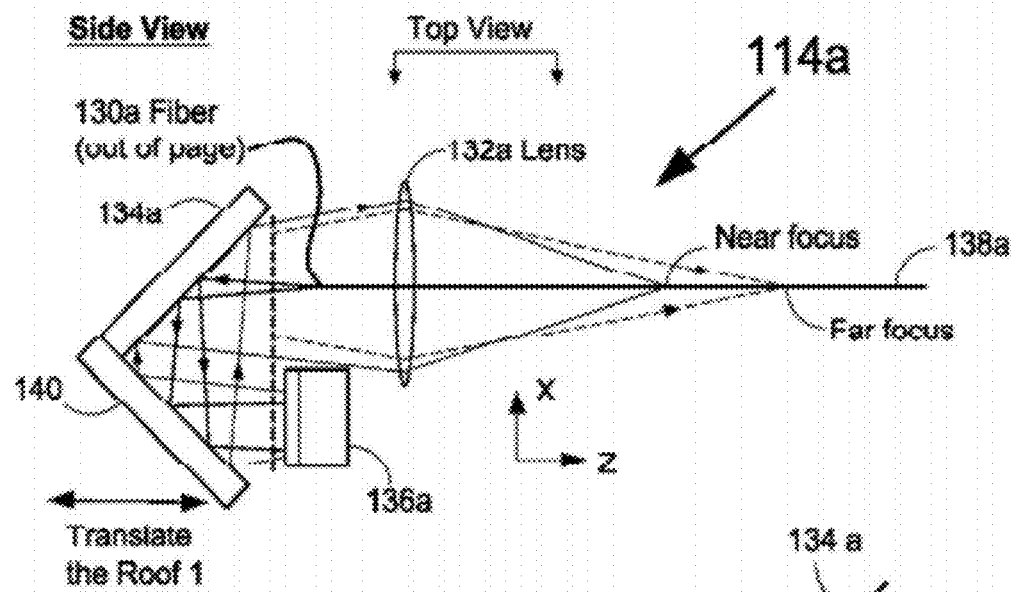
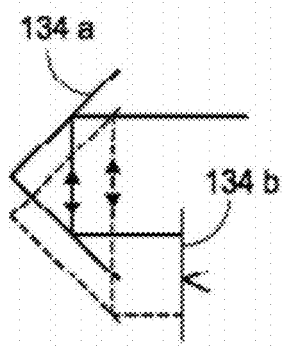
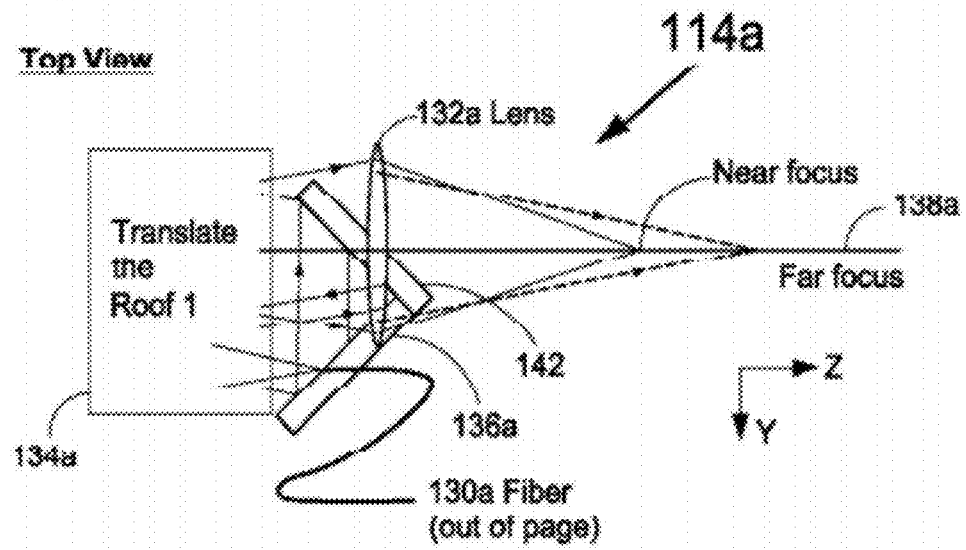

APPARATUS, OPTICAL ASSEMBLY, METHOD FOR INSPECTION OR MEASUREMENT OF AN OBJECT AND METHOD FOR MANUFACTURING A STRUCTURE

RELATED APPLICATION/CLAIM OF PRIORITY

This application is related to and claims priority from provisional application Ser. No. 61/455,768, filed Oct. 25, 2010, which provisional application is incorporated by reference herein.

BACKGROUND

Laser radar is a versatile metrology system that offers non-contact and true single-operator inspection of an object (often referred to as a target). Laser radar metrology provides object inspection that is particularly useful in acquiring high quality object inspection data in numerous industries, such as aerospace, alternative energy, antennae, satellites, oversized castings and other large-scale applications.

Known concepts for Laser radar systems are disclosed in U.S. Pat. Nos. 4,733,609, 4,824,251, 4,830,486, 4,969,736, 5,114,226, 7,139,446, 7,925,134, and Japanese Patent #2,664,399 which are incorporated by reference herein. The laser beam from the laser radar system (referred to herein as the "measurement beam") is controlled by the laser radar system optics, and is directed from the laser radar system and at the target. The laser beam directed from the laser radar system may pass through a splitter which directs the laser beam along a measurement path and at the target, and splits off a portion of the laser beam to a processing system that is disclosed in U.S. Pat. Nos. 4,733,609, 4,824,251, 4,830,486, 4,969,736, 5,114,226, 7,139,446, 7,925,134, and Japanese Patent #2,664,399, and forms no part of the present invention. The laser beam directed along the measurement path is reflected from or scattered by the target, and a portion of that reflected or scattered laser beam is received back at the laser radar system, where it is detected and processed to provide information about the target. The detection and processing of the reflected or scattered light is provided according to U.S. Pat. Nos. 4,733,609, 4,824,251, 4,830, 486, 4,969,736, 5,114,226, 7,139,446, 7,925,134, and Japanese Patent #2,664,399, which are incorporated by reference and form no part of the present invention. The present invention is directed at the optical assembly by which a pointing beam and measurement laser beam are transmitted from the laser radar system.

An existing laser radar system has a relatively large rotating scanning (pointing) mirror, that rotates relative to other parts of the laser radar system, and is used to achieve beam pointing. This mirror causes system instability and polarization issues. The existing system is also not achromatic, so the two wavelengths (e.g. the pointing beam wavelength and the measurement beam wavelength) cannot be focused on a part in space simultaneously. In addition, the existing system limits the field of view of the camera that is pointed in the same direction as the laser radar.

SUMMARY OF THE PRESENT INVENTION

The present invention has been made taking the circumstances as described above into consideration, an object of which is to provide an apparatus comprising an optical assembly moveable as a unit as part of an apparatus, and configured to direct a measurement beam through an outlet of an optical assembly, an optical assembly configured to fold a optical path of the measurement beam that is being directed through the outlet of the optical assembly.

Another object of the present invention is to provide an optical assembly for focusing a beam along a line of sight, comprising a lens, a scanning reflector and a fixed reflector that co-operate to focus a beam from a light source along a line of sight that extends through the lens, where the lens, the scanning reflector and the fixed reflector are oriented relative to each other such that a beam from the light source is reflected by the scanning reflector to the fixed reflector, and reflected light from the fixed reflector is reflected again by the scanning reflector and directed along the line of sight through the lens, and wherein the scanning reflector is moveable relative to the source, the lens and the fixed reflector, to adjust the focus of the beam along the line of sight.

Another object of the present invention is to provide a method for inspection or measurement of an object, pointing a measurement beam at an object by using of an optical assembly configured to direct a measurement beam through an outlet of the optical assembly, the optical assembly configured to fold the optical path of the measurement beam that is being directed through an outlet of the optical assembly Still another object of the present invention is to provide a method for manufacturing a structure, comprising: producing a structure based on design information; obtaining shape information of structure by using of the apparatus; obtaining shape information of a structure by arranging a produced structure; comparing a obtained shape information with a design information.

Additional features of the present invention will become apparent from the following detailed description and the accompanying drawings.

BRIEF DESCRIPTION OF THE DRAWINGS

FIG. 7a is a schematic illustration of one version of an optical assembly according to second embodiment;

FIG. 7b is a fragmentary, schematic illustration of the optical assembly of FIG. 7a, showing the reflection schema provided by the corner cube and the plane mirror;

FIGS. 8a and 8b are schematic side and top illustrations of second version of an optical assembly according to second embodiment;

FIG. 8c is a fragmentary, schematic illustration of the optical assembly of FIGS. 8a and 8b, showing the reflection schema provided by the reflective roofs of those elements.

DETAILED DESCRIPTION

Figure 1:
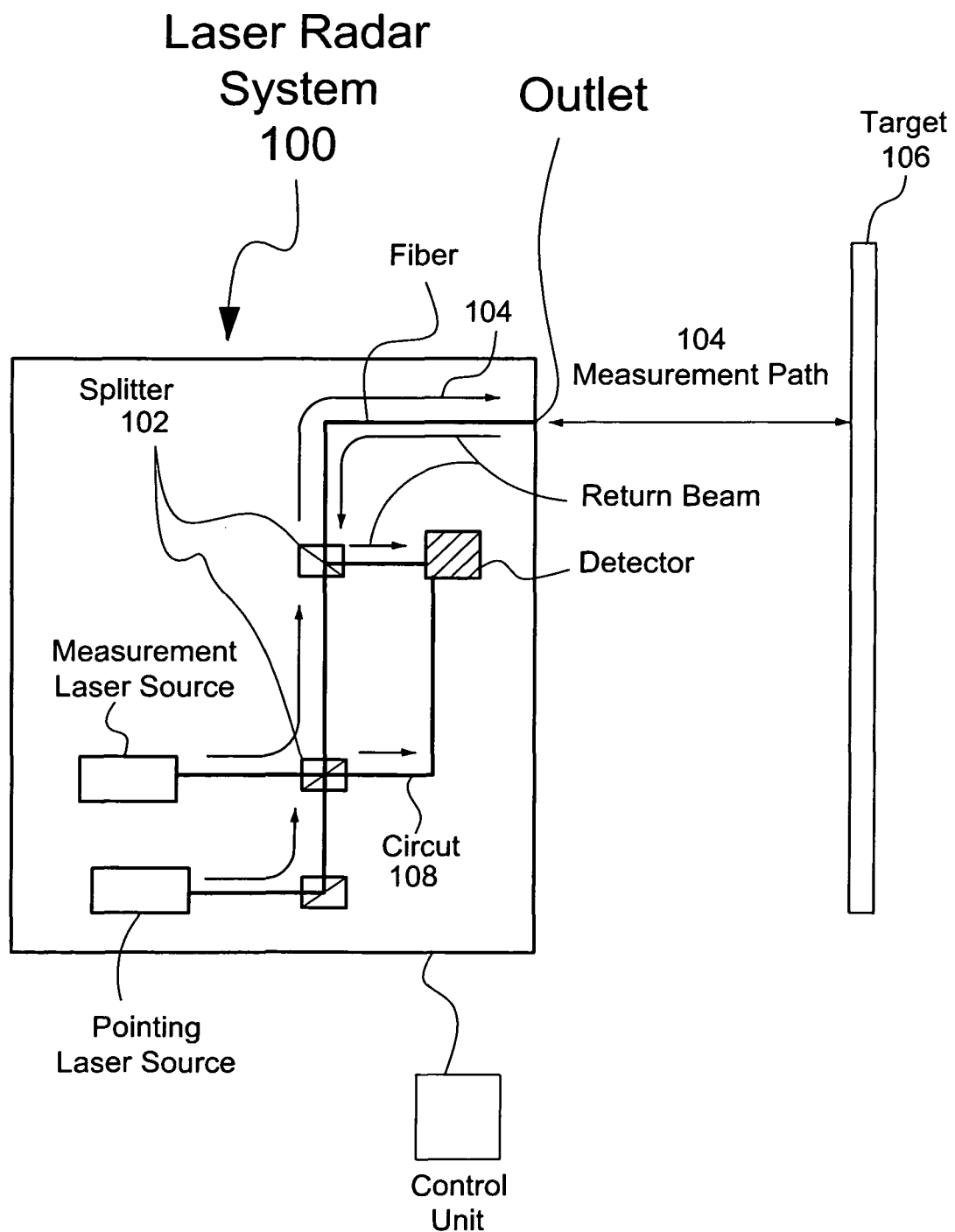
FIG. 1 is a schematic illustration of a laser radar system, of a type that can employ an optical assembly according to embodiment.

Embodiments of the laser radar system 100 according to the present invention will be explained below with reference to the drawings. However, the present invention is not limited thereto.

The present embodiments provides a compact optical assembly (sometimes referred to as an Integrated Optical Assembly, or IOA), that is useful in a laser radar system, and is also useful in various other optical systems.

In a laser radar system, the optical assembly is configured to move as a unit with the laser radar system, as the laser radar system is pointed at a target, and eliminates the need for a large scanning (pointing) mirror that is moveable relative to other parts of the laser radar system.

The optical assembly is designed to be compact, and to utilize a relatively simple assembly of elements for directing and focusing a pointing beam and a measurement beam at an outlet of the optical radar system.

An optical system according to a first embodiment comprises catadioptric optical optics that is moveable as a unit with the laser radar, and directs both a pointing beam and a measurement beam at a target at which the laser radar system is pointed, while eliminating the need for a scanning (pointing) mirror that is moveable relative to other components of the laser radar to direct the pointing beam. The pointing beam is produced in a visible (e.g. red such as around 610 nm to 750 nm) wavelength range, and the measurement beam is produced in a different, predetermined wavelength range (e.g. infra red such as around 0.7 µm to 10 µm, or IR). The pointing and measurement beams are handled by the compact optical assembly of the present embodiment which moves as a unit with the laser radar system, to direct the pointing and measurement beams from the laser radar system (and at the target), in a manner that avoids use of a scanning (pointing) mirror that is moveable relative to other components of the laser radar.

The optical assembly includes catadioptric optics that include a concave mirror that provides most of the optical power, and allows easier achromatization between the two required wavelengths. The concave mirror folds the optical path onto itself, reducing the overall size of the optical assembly substantially. The size of the optical assembly is designed to be small enough to allow a camera to be located on the moving part of the laser radar system, and eliminates parallax effects by use of a reflective window or cold mirror that allows the camera optical axis to be collinear with the axis of the measurement beam. The concave mirror helps achromatize the system, while also folding the optical path to create a compact optical system which allows the entire optical assembly to be rotated as a unit with the laser radar system for scanning, eliminating the expensive and troublesome rotating (pointing) mirror of the existing system.

Basically, the first embodiment comprises an optical assembly moveable as a unit as part of a laser radar system, and configured to direct a pointing beam and a measurement beam through an outlet of the laser radar system. The optical assembly includes catadioptric optics configured to fold the optical path of the pointing beam and measurement beam that is being directed through the outlet of the laser radar system, to compress the size of the optical assembly.

The first embodiment can be implemented in various ways. For example, the optical assembly includes a window with a transmissive portion through which the pointing beam and measurement beam are directed to the outlet of the laser radar system. A relay system directs the pointing beam and measurement beam from an optical fiber to a reflective area of the window, and the catadioptric optics receive and reflect the pointing beam and measurement beam from the reflective area of the window back through a transmissive portion the window, to fold the optical path of the pointing beam and measurement beam that is being directed through the outlet of the laser radar system, to compress the size of the optical assembly. The concave mirror folds the optical path onto itself. In other words, part of the optical path overlaps. As for the optical path for the measurement beam, the optical path between concave mirror and reflective area of the window overlaps. In other words, optical assembly has more than two derections of a light from light source.

In one specific version of this implementation, the optical assembly includes at least one moveable optic to vary focus of the pointing beam and the measurement beam that is reflected by the catadioptric optics and directed back through the transmissive portion of the window. In another specific version, the focus of the pointing beam and measurement beam that is reflected by the catadioptric optics and directed back through the transmissive portion of the window is changed by moving a plurality of optics, the plurality of optics characterized by low optical power but a large amount of spherical aberration.

In another implementation of the first embodiment the window comprises a cold mirror that transmits light in a predetermined wavelength range that includes the wavelength range of each of the pointing and measurement beams, and an optical fiber that transmits the pointing beam and the measurement beams is located at a central location of the cold mirror. The catadioptric optics receive the pointing beam and the measurement beam from the optical fiber and reflect the pointing beam and the measurement beam back through the cold mirror, where it is directed to the outlet of the laser radar system. The camera 140 is placed such that it accepts light reflected by the coating on cold mirror 122, allowing the line of site of the camera to be collinear with the axis of the measurement and pointing beams. The cold mirror 122 allows the camera optical axis to be collinear with the axis of the measurement beam.

In one specific version of this implementation, the optical assembly includes at least one moveable optic to vary focus of the pointing beam and the measurement beam that is reflected by the catadioptric optics and directed back through the cold mirror. In another specific version, the focus of the pointing beam and measurement beam that is reflected by the catadioptric optics and directed back through the cold mirror is changed by moving a plurality of optics, the plurality of optics characterized by low optical power but a large amount of spherical aberration.

According to a basic aspect of a second embodiment of the present invention, the optical assembly is configured to direct a pointing beam and a measurement beam along a line of sight and through an outlet of the laser radar system. The optical assembly comprises a light source, a lens, a scanning reflector and a fixed reflector that co-operate to focus the pointing and measurement beams from the light source along a line of sight that extends through the lens. The light source, the lens, the scanning reflector and the fixed reflector are oriented relative to each other such that the pointing and measurement beams from the light source are reflected by the scanning reflector to the fixed reflector, and reflected pointing and measurement beams from the fixed reflector are reflected again by the scanning reflector and directed along the line of sight through the lens, and the scanning reflector is moveable relative to the source, the lens and the fixed reflector, to adjust the focus of the pointing and measurement beams along the line of sight.

According to a preferred version of the second embodiment, the scanning reflector comprises a retroreflector, and the fixed reflector comprises a plane mirror. The source, the lens and the plane mirror are all in fixed locations relative to a support structure for the optical assembly, and the retroreflector is moveable relative to those fixed locations, to vary the focus of the pointing and measurement beams along the line of sight.

The following detailed description also provides several versions of the optical assembly of the second embodiment. In one version, the retroreflector comprises a corner cube that has at least three reflective surfaces that are oriented so that (i) the pointing and measurement beams from the source are reflected through the corner cube to a plane mirror, (ii) the pointing and measurement beams reflected from the plane mirror are again reflected through the corner cube, and (iii) movement of the corner cube in at least one predetermined direction adjusts the focus of the pointing and measurement beams along the line of sight, in a manner that is substantially unaffected by movement of the corner cube in directions transverse to the predetermined direction or by rotations of the corner cube relative to the predetermined direction.

In another version of an optical assembly according to the second embodiment, the scanning reflector comprises a reflective roof that provides two reflections of the pointing and measurement beams, and the fixed reflector comprises a reflective roof that also provides two reflections of the pointing and measurement beams, where the nodal lines of both reflective roofs are in a predetermined orientation relative to each other.

The following detailed description also provides concepts for configuring and orienting the components of the optical assembly (e.g. for the second embodiment). Those concepts are designed, e.g. to reduce the weight of the optical assembly, and improve the performance of the optical assembly, while keeping the optical assembly as compact as possible.

In one concept, the pointing and measurement beams reflected by the scanning reflector and directed along the line of sight through the lens, are reflected by a fold mirror that folds the line of sight of the pointing and measurement beams directed through the lens. The source comprises an optical fiber supported by the fold mirror.

In another concept, the lens, the beam source and the plane mirror are supported in a manner such that they can move as a unit relative to the retroreflector, and wherein the line of sight moves with the unit.

In still another concept, the pointing and measurement beams reflected by the scanning reflector and directed along the line of sight through the lens are reflected by a polarization beam splitter that folds the line of sight of the pointing and measurement beams directed through the lens, and wherein the source comprises an optical fiber in a predetermined location relative to the polarization beam splitter that folds the line of sight of the pointing and measurement beams directed through the lens.

In yet another concept, the source comprises an optical fiber supported by a monolithic member that has a portion that functions as the plane mirror and another portion that folds the line of sight of the pointing and measurement beams reflected by the scanning reflector and directed along the line of sight through the lens.

In still another concept, the source comprises an optical fiber supported by a transmissive member that also supports the plane mirror.

First Embodiment

As described above, the present invention provides an optical assembly that is moveable as a unit with a laser radar system, and is configured to transmit a pointing beam and a measurement beam from the laser radar system, where they can be directed at a target at which the laser radar system is pointed. The present invention is described herein in connection with a laser radar system of the type described in U.S. Pat. Nos. 4,733,609, 4,824,251, 4,830,486, 4,969,736, 5,114,226, 7,139,446, 7,925,134, and Japanese Patent #2,664,399, which are incorporated herein by reference, and from that description, the manner in which the present invention can be implemented with various types of laser radar systems will be apparent to those in the art.

Figure 2:
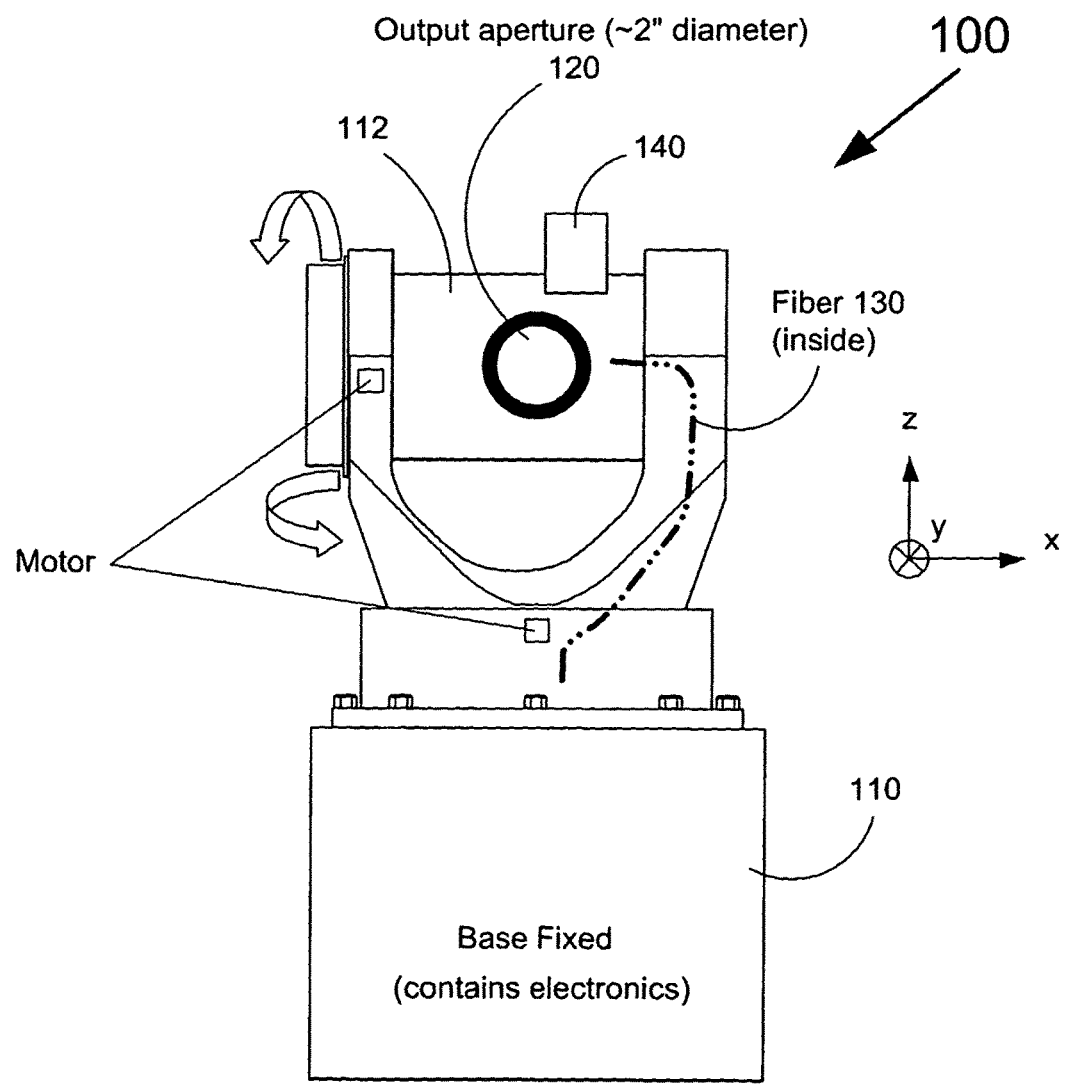
FIG. 2 is a front view of a preferred type of laser radar system that can employ an optical assembly according to embodiment.

FIGS. 1 and 2 show a laser radar system that includes all of the embodiments disclosed in this application. As shown in FIGS. 1 and 2, a laser radar system 100 produces a point beam in a visible (e.g. red) wavelength range, and a measurement beam in a different (e.g. infra red, IR) wavelength range, and directs (transmits) the pointing and measurement beams to an outlet 120 of the laser radar system. The pointing beam is used to identify a point on a target 106 at which the measurement beam is directed. The laser source of the pointing beam and the measurement beam is different. A control unit can control a laser radar system 100. In this embodiment, the laser radar system 100 has a control unit. However a separate system coupled with the laser radar system 100 may have the control unit.

The measurement beam may pass through a splitter 102 which directs the measurement beam (and the pointing beam) along a measurement path 104 and at the target 106, and sends a portion of the measurement beam through a circuit 108 where that portion of the laser beam is processed in a manner described in U.S. Pat. Nos. 4,733,609, 4,824,251, 4,830,486, 4,969,736, 5,114,226, 7,139,446, 7,925,134, and Japanese Patent #2,664,399. In FIG. 1, that splitter is the bottom splitter identified by 102. The measurement beam directed along the measurement path 104 is reflected from the target 106 and a portion of that reflected or scattered measurement beam is received back at the laser radar system 100, where it is directed to a detector by the top splitter shown in FIG. 1, detected and processed to provide information about the target 106. The detection and processing of the reflected or scattered radiation from the measurement beam is provided in a base 110 of the laser radar system 100, and is configured to detect and process the reflected radiation according to U.S. Pat. Nos. 4,733,609, 4,824,251, 4,830,486, 4,969,736, 5,114,226, 7,139,446, 7,925,134, and Japanese Patent #2,664,399, which are incorporated by reference and form no part of the present embodiments. Briefly, optical heterodyne detection provides a source light beam which is directed to a target 106 and reflected therefrom. The return light beam is then mixed with a local oscillator light beam on a photo detector to provide optical interference patterns which may be processed to provide detailed information about the target 106. Optical heterodyne techniques take advantage of the source and reflected light beam reciprocity. For example, these light beams are substantially the same wavelength and are directed over the same optical axis. Measurement path 104 and target path 104 is same. This provides an improved signal-to-noise ratio (SNR) and heightened sensitivity. The SNR is sufficiently high so that a small receiving aperture may be used, in contrast to known direct detection systems. A small receiver aperture may be envisioned as a very small lens capable of being inserted into limited access areas. Since a small receiver aperture can still provide detailed information about the target, the optical components of a coherent system may be made very small and provide related increases in scanning speed and accuracy. For example a coherent optical system using a one-half inch aperture can obtain more information about a target than a four inch aperture used in a direct optical detection system. The present invention is directed at the optical assembly by which the pointing beam and measurement beam are transmitted to the outlet 120 of the laser radar system.

In a known laser radar system, a moveable mirror is provided for directing the point beam at a target. The moveable mirror is separate from the optics that transmit the measurement beam, and requires a relatively large laser radar housing to accommodate both the moveable mirror and the laser radar optics. The present invention is relatively compact, because both the measurement beam and pointing beam are produced by a relatively compact optical assembly that can move as a unit with the laser radar system 100. Moreover, the optical assembly of the present invention is designed to be relatively stable in performing its beam transmission/reception functions. An electronic motor is provided for moving the optical assembly. In this embodiment, The optical assembly is movable for two axis relative to different direction. The two axis is located with YX plane and XY plane as shown FIG. 2. The two axis are the Z axis and X axis. The encoder is provided for monitoring the position of the optical assembly. The control unit can control power of the electronic motor by the position of the optical assembly.

As shown in FIG. 2, the laser radar system 100 includes a housing (e.g. a rotatable cylinder 112) in which the optical assembly is located and secured, so that the optical assembly moves as a unit with the cylinder 112 relative to the base 110 of the laser radar system. The laser radar system includes an outlet 120 in the housing 112, and through which radiation (e.g. in the two wavelengths of the pointing and measurement beams) is directed from the laser radar system. The base 110 contains the processing features of the laser radar system, that are disclosed in U.S. Pat. Nos. 4,733,609, 4,824,251, 4,830,486, 4,969,736, 5,114,226, 7,139,446, 7,925,134, and Japanese Patent #2,664,399.

Figure 3A:
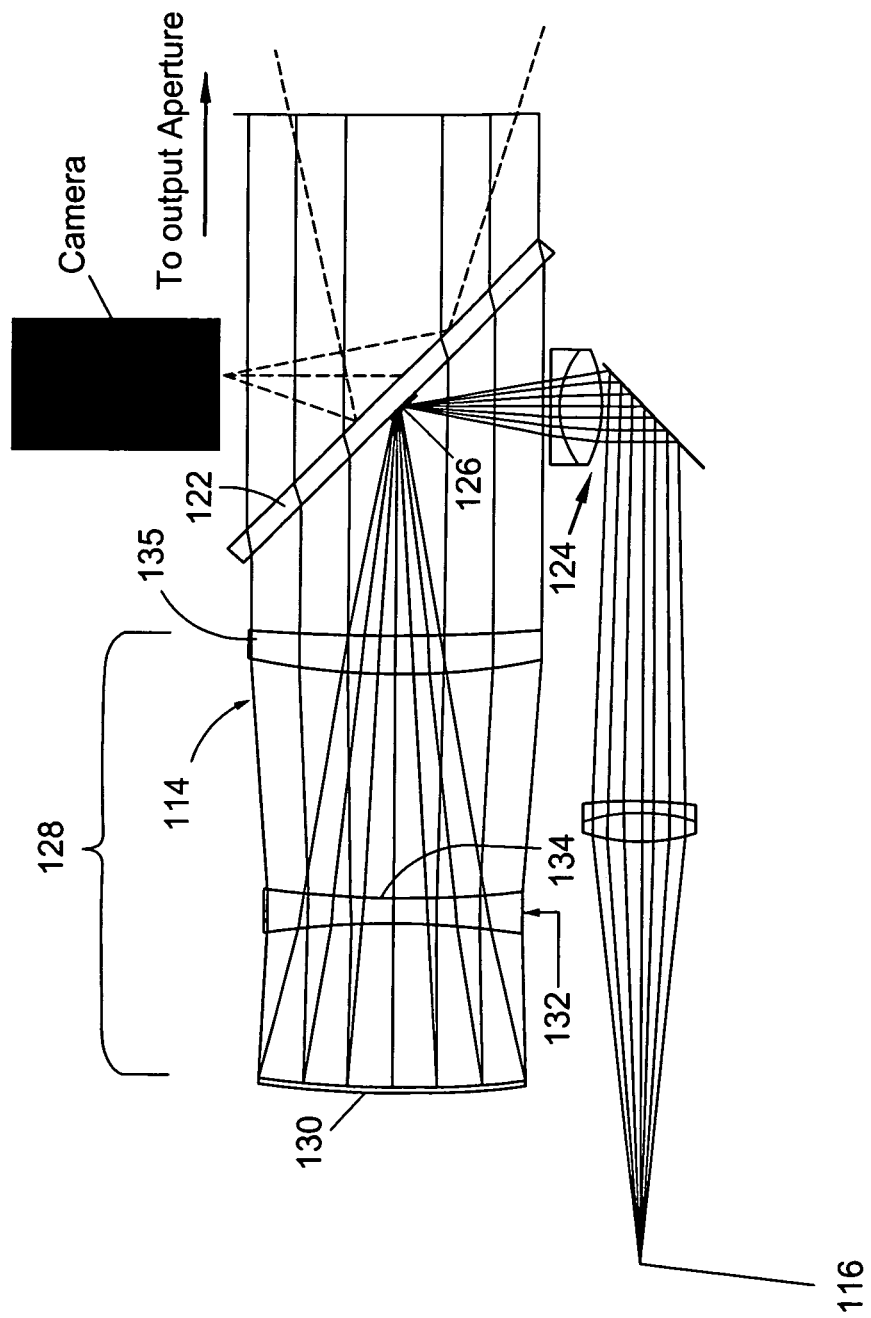
FIGS. 3(A), 3(B) and 3(C) are examples of different versions of an optical assembly according to first embodiment.
Figure 3B:
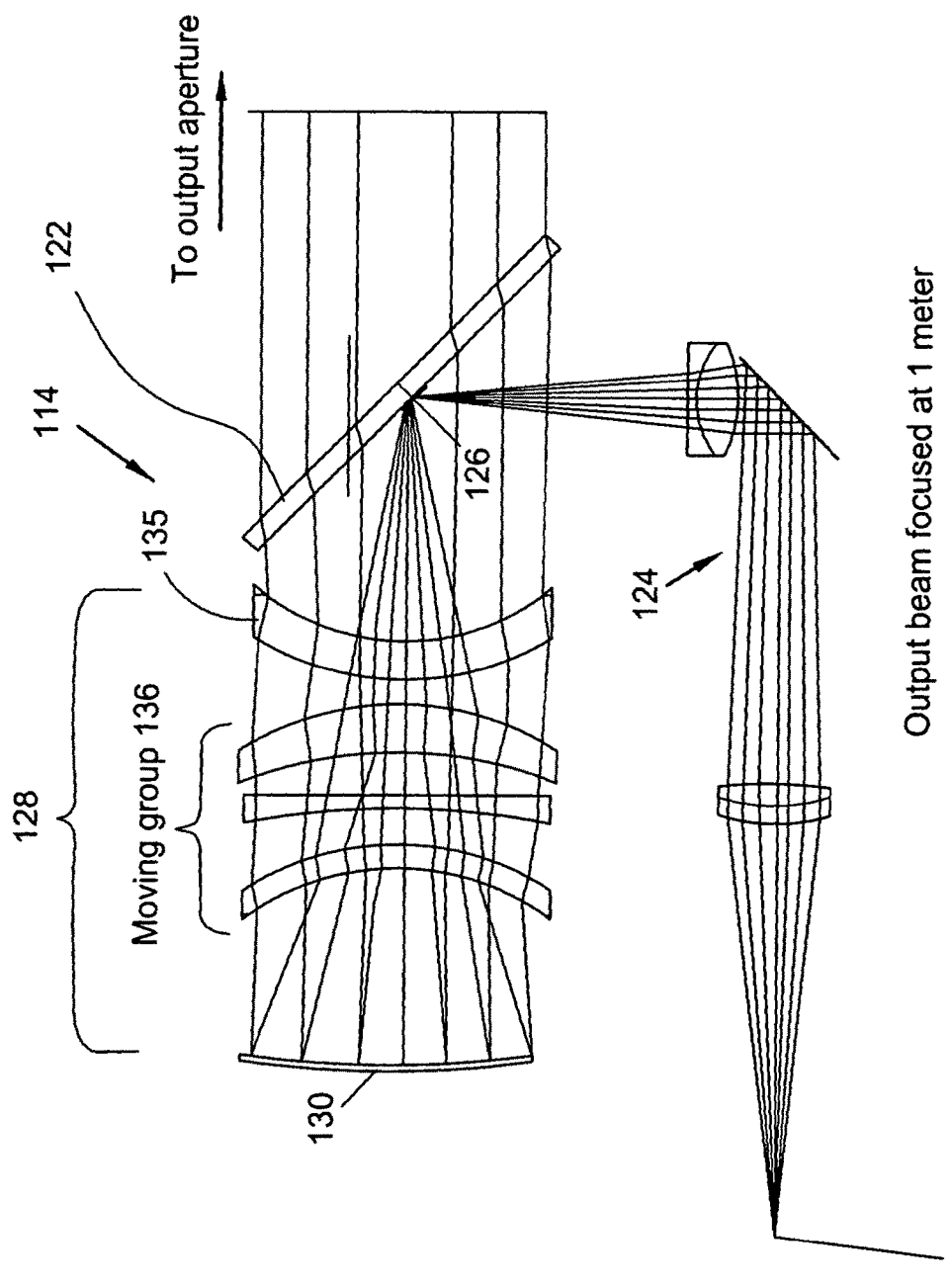
Figure 3C:
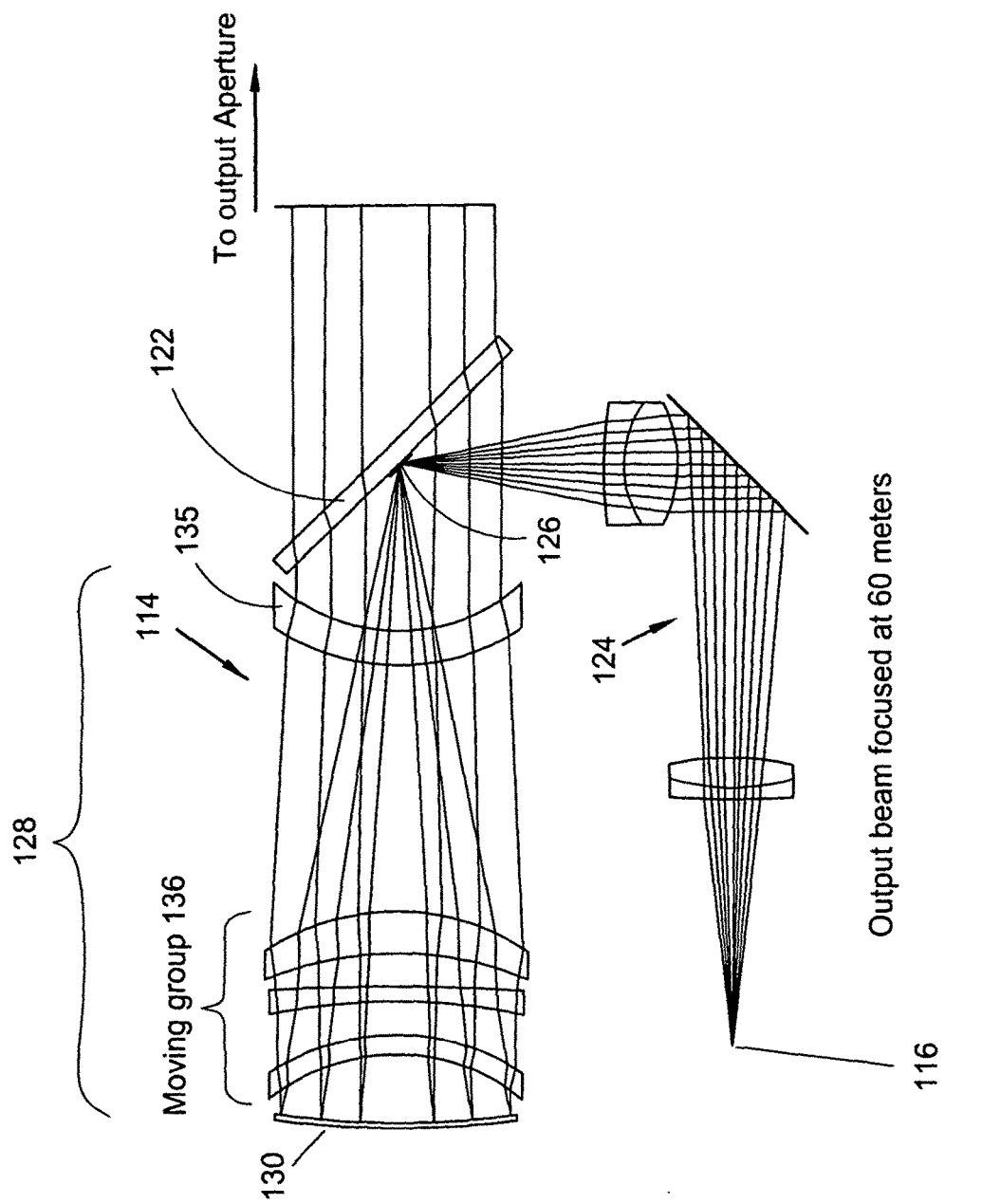

The basic features of an optical assembly 114 of a first embodiment of the present embodiments can be appreciated from FIGS. 3(A) through 3(C). In FIG. 3(A), the optical assembly 114 includes an optical fiber (represented by fiber tip 116) through which a pointing beam and measurement beam are transmitted, a relay system 124 that directs the pointing and measurement beams from the optical fiber 116 to a small reflective area 126 of a window 122 (also referred to as a fold mirror in the embodiments of FIGS. 3(A) through 3(C)), and catadioptric optics 128 that receive and reflect the pointing and measurement beams from the reflective area 126 of the window 122 back through the window 122, where it is directed through the outlet 120 of the housing 112. The window 122 has a small silvered area on one side that forms the reflective area 126, and a coating on its other side that allows radiation in the red and infra red range to be transmitted through the window and to the output aperture 120. The camera 140 is placed such that it accepts light reflected by the coating on window 122, allowing the line of site of the camera to be collinear with the axis of the measurement and pointing beams. It should be noted that while the location and orientation of camera 140 is shown in FIG. 3(A), the camera 140 could be similarly located and oriented relative to the window 122 in the versions of the first embodiments shown in FIGS. 3(B), 3(C) and 4.

In addition, the optical assembly 114 is configured to receive at least some radiation that is reflected or scattered from the target 106, and directs that radiation back through the fiber 116. The fiber 116 can have a fiber beam combiner that combines a pointing beam in the visable (e.g. red) wavelength range with the measurement beam in the different, e.g. infra red (IR) wavelength range. The pointing beam and measurement beams are generated from separate sources, and are combined by a fiber beam combiner located inside the base 110 in a manner well known to those in the art.

The laser radar system 100 of this embodiment has the pointing beam and measurement beam. However the laser radar system 100 may have the measurement beam without the pointing beam. For example, the measurement beam is in the visible. Therefore, in this case, the measurement beam can also be the pointing beam. The laser radar system 100 of this embodiment has the different wavelength region between the pointing beam and measurement beam. However the laser radar system 100 may have the same wavelength region such as the visible region.

In FIG. 3(A), the optical assembly 114 includes the relay system 124 that directs the pointing and measurement beams from the optical fiber 116 to the small reflective area 126 of the window 122, and catadioptric optics 128 that receive and reflect the pointing and measurement beams from the reflective area 126 of the window 122 back through the transmissive portion of the window 122, where it is directed through the outlet 120 of the housing. The catadioptic optics 128 include a spherical mirror 130 from which radiation (i.e. from the pointing and measurement beams) is reflected and one or more optics through which the radiation is directed. In the embodiment of FIG. 3(A), the optical assembly includes at least one moveable optic 132 to vary focus of the radiation that is reflected from the spherical mirror 130 and back through the window 122. The optic 132 may be bi concave, or may be plano concave, with at least one concave portion 134 facing the fold mirror 122. The moveable optic 132 is configured to focus the radiation reflected from the spherical mirror 130 at the target, and is also configured for reducing stray radiation reflected by transmissive lens surfaces (ghost images) from being directed back through the fiber 116. Specifically, the concave portion 134 of the optic 132 has a center of curvature that is far from the fiber conjugate, to reduce the likelihood of stray radiation reflected by lens surfaces being directed back through the fiber. Also, a lens 135 that is fixed in relation to the optical assembly corrects for spherical aberration, allowing for a diffraction limited focused spot at the target. The spherical mirror folds the optical path onto itself. In other words, part of the optical path overlaps. As for the optical path for the measurement beam, the optical path between concave mirror and reflective area 126 overlaps. In otherworlds the travel direction of light from light source changes in the optical assembly. The direction from reflective area 126 to concave mirror is different from the direction from concave mirror to reflective area 126. In another specific version of the first embodiment, shown in FIGS. 3B and 3C, the optical assembly includes a set 136 of optics that that can move as a group relative to the spherical mirror 130 and the window 122. In the embodiment of FIGS. 3B and 3C, the focus of the pointing beam and measurement beam that is reflected by the catadioptric optics and directed back through the window 122 is changed by moving the set 136 of optics, which are characterized by low optical power but a large amount of spherical aberration. Thus, in the example of FIG. 3B, the set of optics 136 are relatively close to the window 122 to provide focus at a short distance (e.g. about 1 meter), and in FIG. 3C the set of optics 136 are relatively close to the spherical mirror 130 to provide focus at a relatively longer distance (e.g. about 60 meters). The position of the moving group 136 is continuously variable between these two extremes, allowing the measurement beam and pointing beam to be focused at any distance between, for example, 1 and 60 meters from the laser radar optical assembly.

Figure 4:
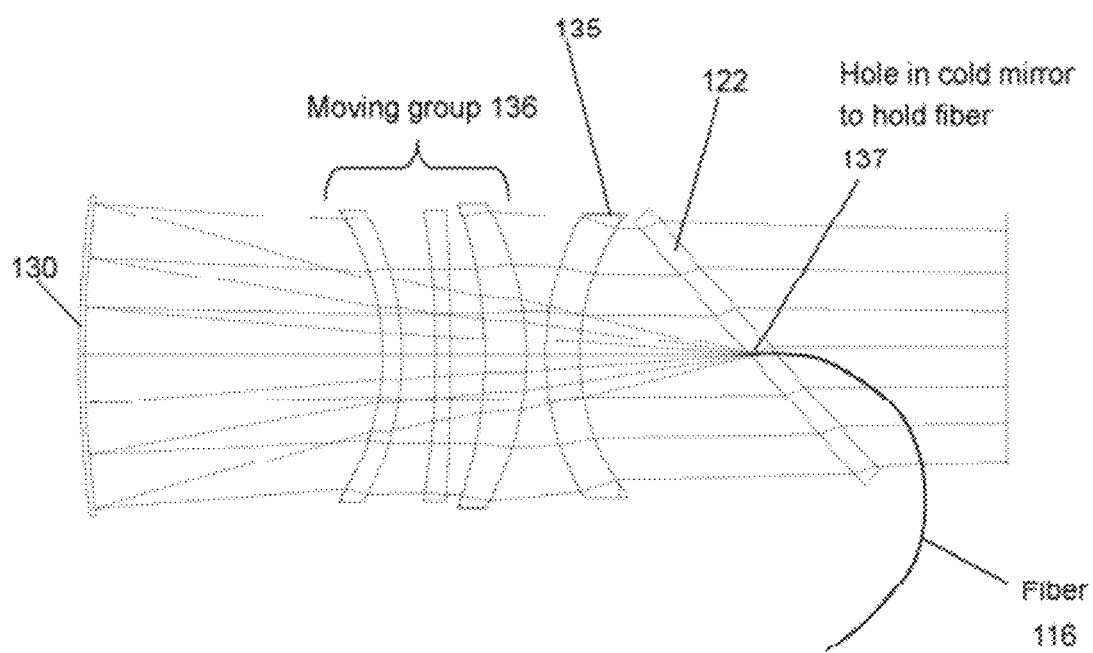
FIG. 4 shows the catadioptric portion of another example of an optical assembly according to first embodiment.

In yet another specific version of the first embodiment, the catadioptric portion of which is shown in FIG. 4, window 122 comprises what is known as a "cold mirror" because it transmits radiation the visible red and IR wavelength ranges of the pointing and measurement beams, and reflects radiation at shorter wavelengths. The optical fiber 116 is located at a hole 137 in a central location of the cold mirror 122, and the catadioptric optics receive the radiation of the pointing and measurement beams from the optical fiber 116 and reflect the radiation back through the cold mirror 122 and to the outlet 120 of the laser radar housing 112, in the manner described in connection with FIGS. 3A, 3B and 3C. That version of the first embodiment can also include the one bi concave or plano concave optic (e.g. as shown at 132 in FIG. 3A) to vary focus of the radiation that is reflected back through the cold mirror (and which has a concave surface 134 with a center of curvature that is far from the fiber conjugate, to reduce stray radiation reflected from the lens surfaces (ghost images) from being directed back through the fiber). Alternatively, that version of the first embodiment can include a plurality of moving optics (e.g. as shown at 136 in FIGS. 3B and 3C) that are configured such that the focus of the pointing beam and measurement beam that is reflected by the catadioptric optics and directed back through the cold mirror 122 is changed by moving the set 136 of optics, which are characterized by low optical power but a large amount of spherical aberration.

Figure 5:
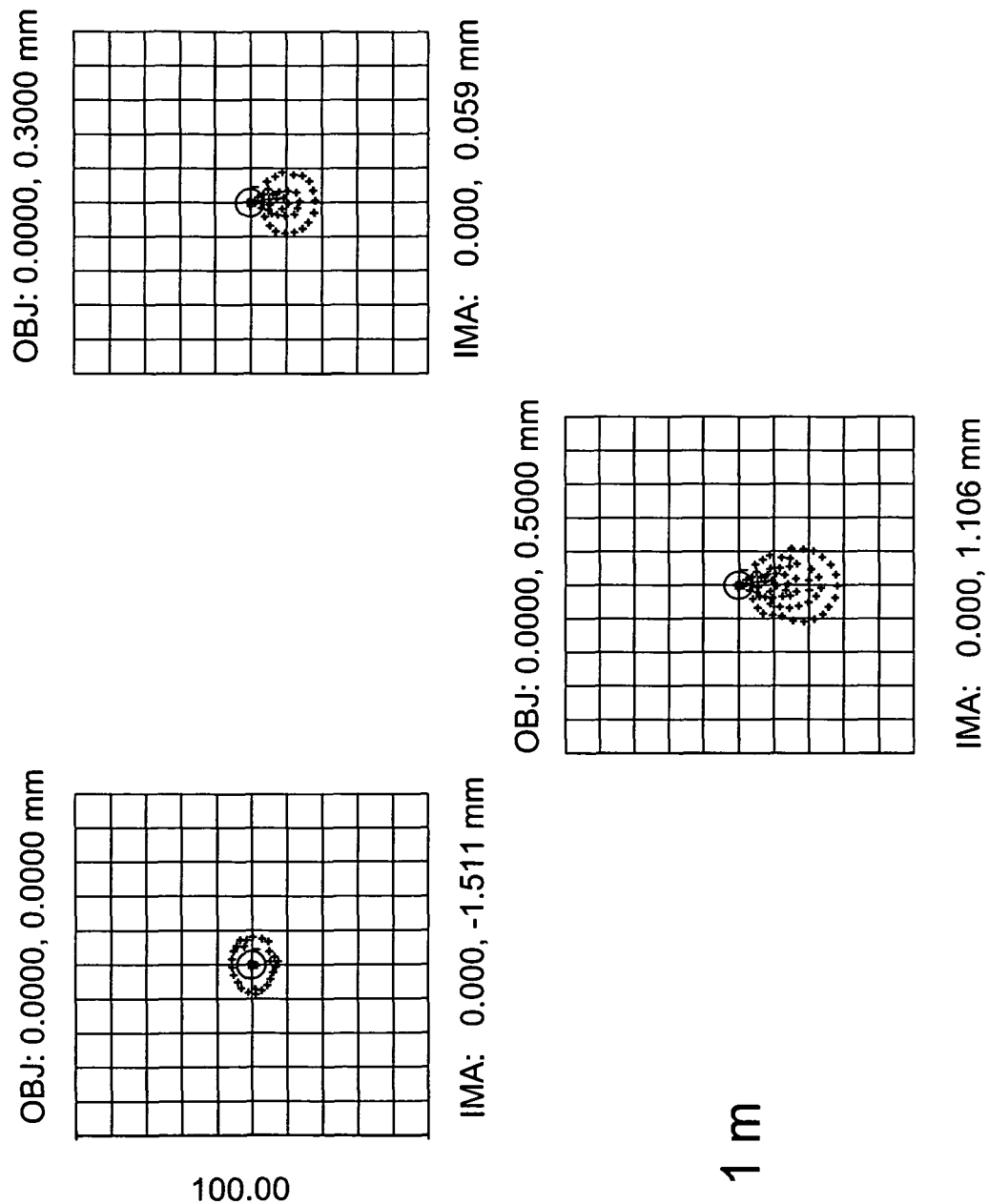
FIG. 5 illustrates certain performance capabilities of an optical assembly according to first embodiment.
Figure 5:
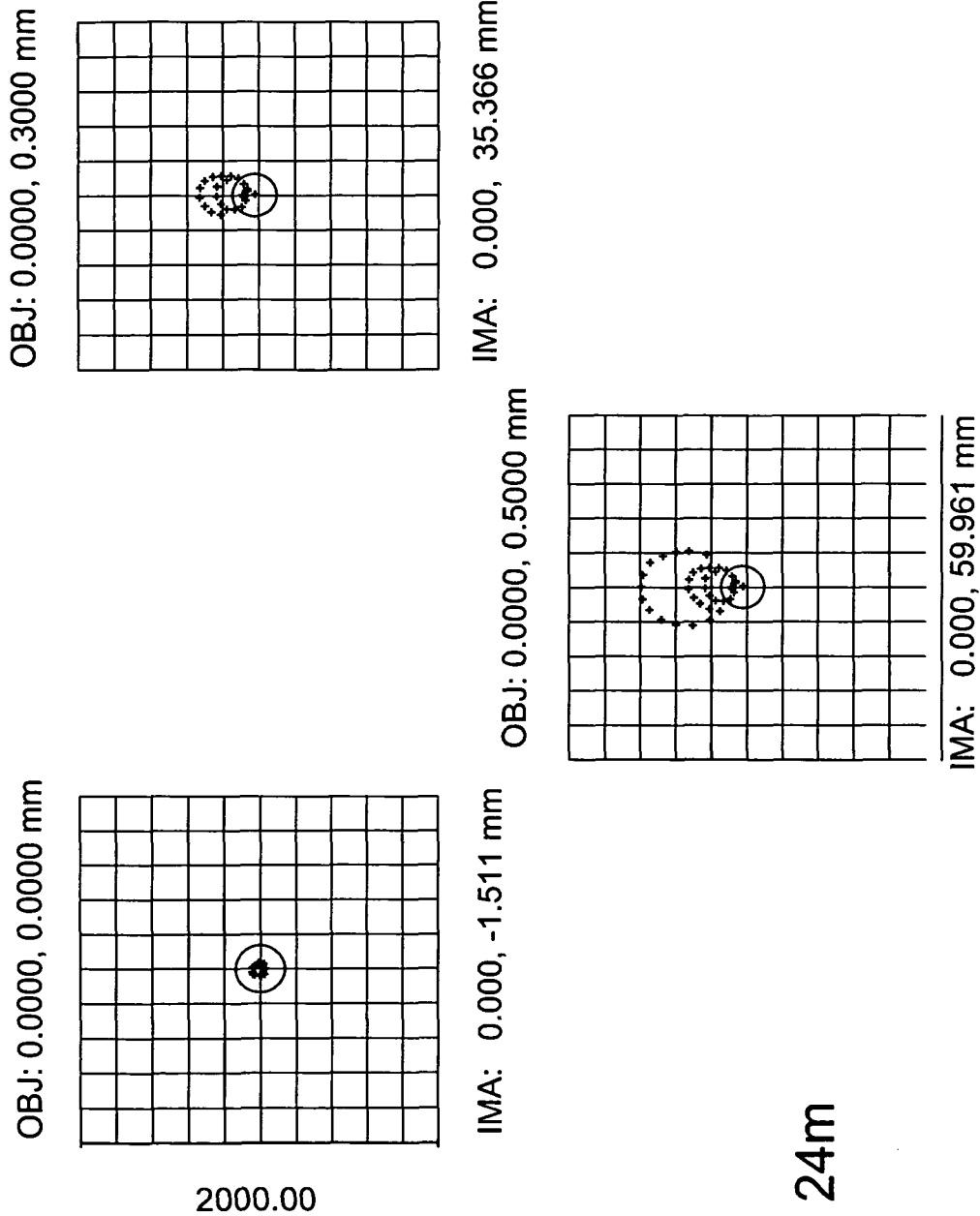
Figure 5:
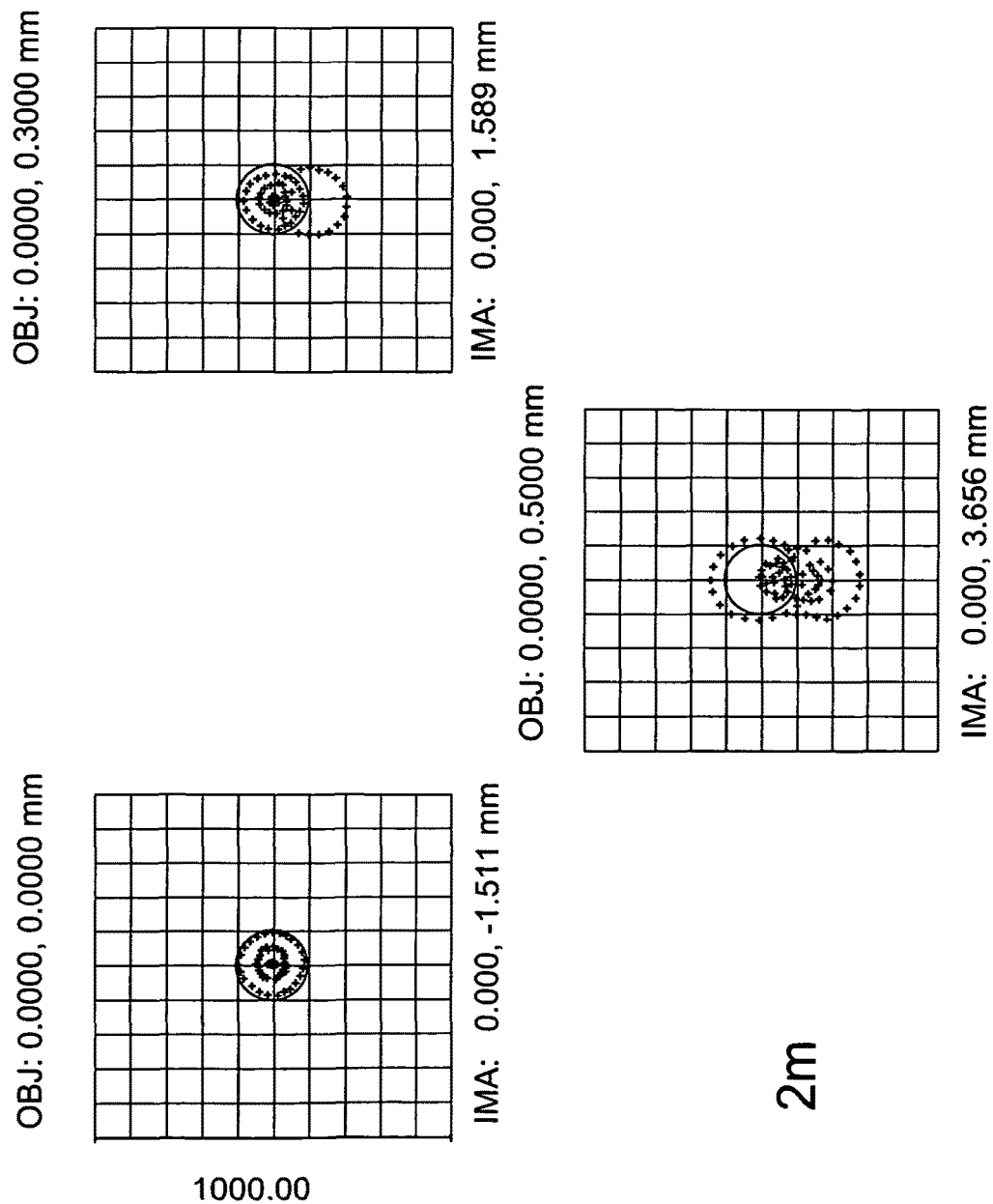
Figure 5:
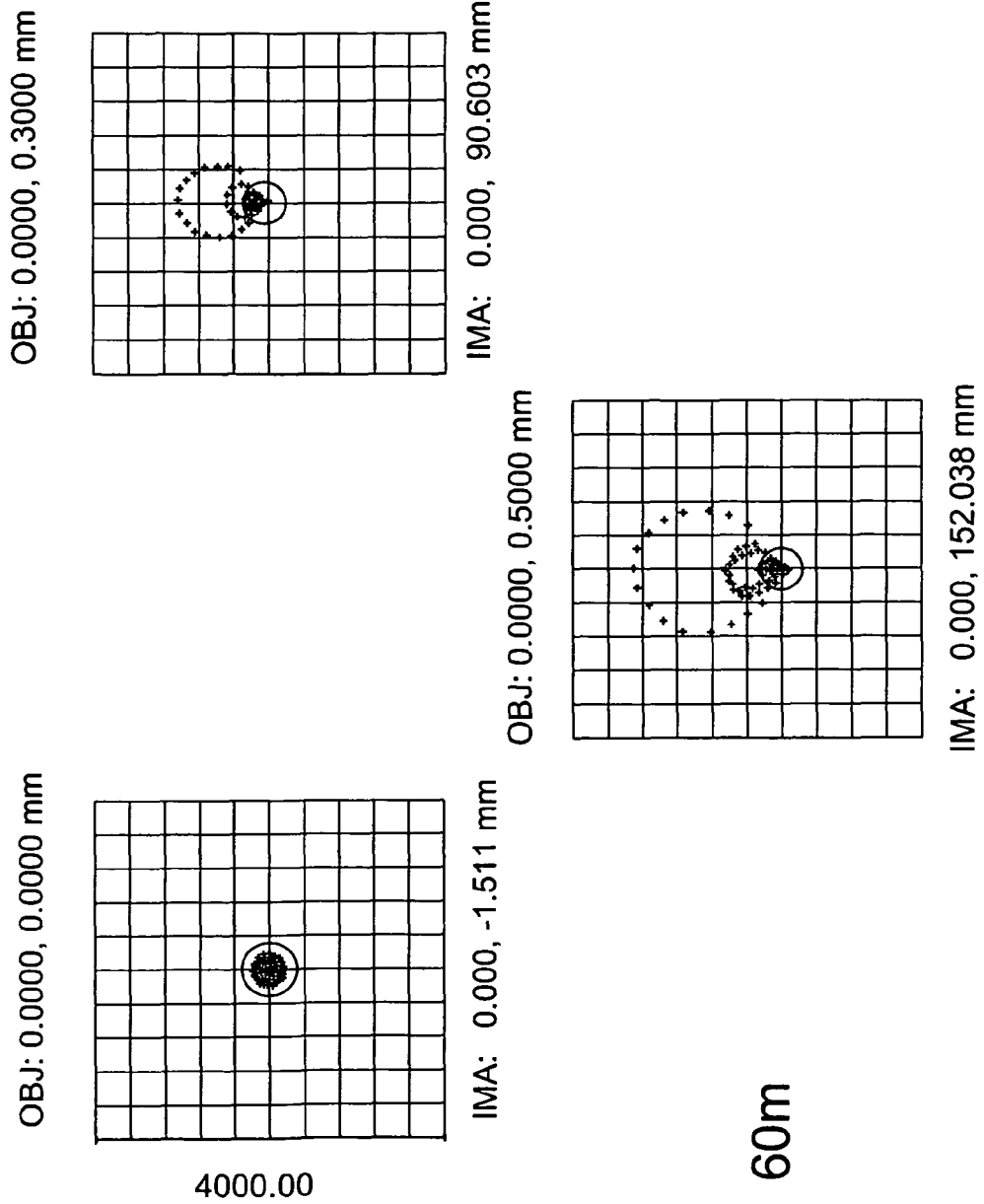

FIG. 5 shows an example of the performance of an optical assembly according to the first embodiment of the present embodiments. In the example of FIG. 5, performance is shown at 1, 2, 5, 24, and 60 meters (for the IR light), where the red light is well focused for all positions. FIG. 5 (and exhibit A) show spot diagrams that indicate the level of performance of the optical system, which should be familiar to those in the art. The solid circles in FIG. 5 (and exhibit A) indicate the diffraction limit as defined by the wavelength and aperture of the laser radar optical system. The diffraction limit represents the best possible performance for this optical system, as is well understood by those in the art. The three plots for each target distance of 1, 2, 5, 24 and 60 meters show the performance as the fiber moves off-axis relative to the catadioptric optical system 128 and/or relay system 124. The three plots for each target distance are for an off-axis distance of 0 mm for the top left, 0.3 mm for the top right and 0.5 mm for the bottom middle. The '+' marks indicate the focused locations of the different rays; if all of these marks are within or close to the circle defining the diffraction limit, then the performance of the lens is diffraction limited, as is well understood by those in the art.

An important aspect of the laser radar's ability to measure the position of the target in three dimensions is the ability to resolve the spot location in a plane perpendicular to the pointing (optical) axis of the laser radar. This is done by accurately measuring the two pointing angles for the steering assembly that points the entire optical assembly. However, in certain situations, the spatial resolution of the target location in the plane perpendicular to the pointing axis can be limited by the size of the spot imaged by the optical assembly at the target. In other words, the smaller the imaged spot of light at the target, the better the position of the target can be determined in three dimensions. So the performance illustrated in FIG. 5 shows that the typical performance achieved using the type of system described in this document can be diffraction limited, as will be clear to those in the art.

In addition, the size of the imaged spot determines how much light can be collected by the optical assembly. If more light is focused onto the target, more light is reflected or scattered by the target and an appropriate fraction of that reflected or scattered light is collected by the optical assembly and focused back to the fiber 116, allowing an accurate measurement of the distance between the laser radar and the target. In other words, a smaller spot allows more measurement light to return to the optical assembly and a more accurate distance measurement to be made, using the techniques described by U.S. Pat. Nos. 4,733,609, 4,824,251, 4,830,486, 4,969,736, 5,114,226, 7,139,446, 7,925,134, and Japanese Patent #2,664,399, which are incorporated by reference herein.

Figure 6:
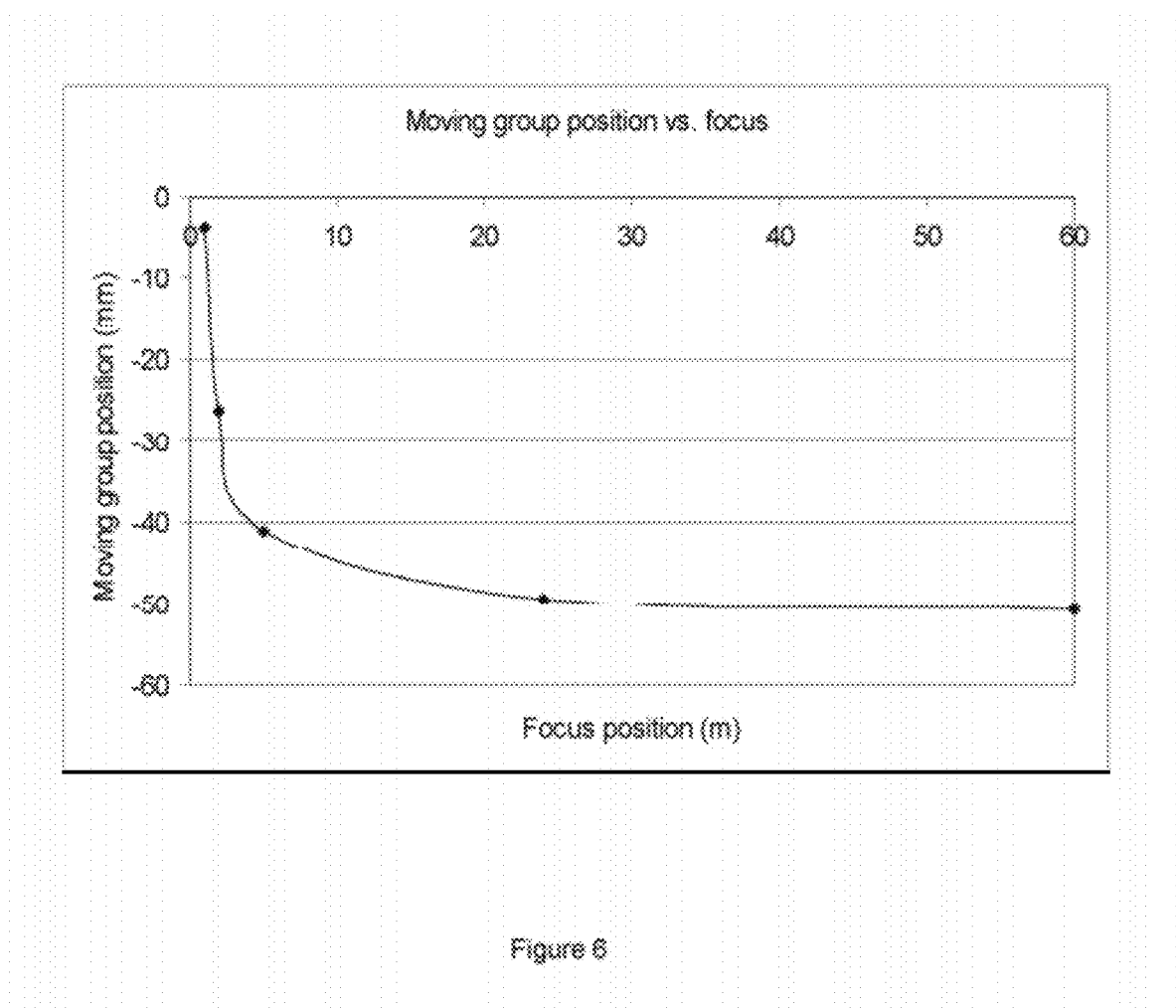
FIG. 6 illustrates additional performance capabilities of an optical assembly according to first embodiment.

FIG. 6 shows an example of the focus location of the measurement and pointing beams as a function of the axial position of the moving group 136, with an optical assembly according to the present embodiments. The plot shown in FIG. 6 shows the moving group position specifically for the configuration shown in FIGS. 3B and 3C, and demonstrates that to go from 1 meter to 60 meters in distance (from the laser radar housing 112 to the target) requires approximately 47 mm of movement of the moveable group of optics 136.

As will be appreciated by those in the art, the optical assembly 114 of the first embodiment is compact and rigid, and uses the concave mirror 130 for much of the optical power. Also, the concave mirror 130 produces no chromatic aberration. In the embodiments of FIGS. 3A-3C, the window 122 has the small silvered region 126 added to one side of the window (creating a small obscuration). The other side of the window 122, would have a wavelength selective coating that transmits light in the predetermined (e.g. visible red, IR) wavelength ranges, and reflects light in the visible part of the spectrum, except for the wavelength used for the visible pointing beam. This allows the camera 140 to use that remaining visible light to view the scene being measured by the laser radar system.

Also, it should be noted that the primary mirror 130 is concave, and in the preferred embodiment, it is spherical. The primary mirror 130 can help achromatize the optical assembly. Focusing can be accomplished by the bi concave or plano concave moving lens 132 in the embodiment of FIG. 3(A). Focusing can also be accomplished by moving the lens group 136 (FIGS. 3B, 3C) between the primary mirror 130 and the cold mirror 122.

Thus, the catadioptric optical assembly of the first embodiment, provides a compact optical assembly, designed to (i) remove the need for a moving mirror (removing problematic doppler effects), (ii) get the two wavelengths (red and IR) in focus simultaneously. The moveable lens 132, or lens group 136, located between the concave mirror 130 and the window (or cold mirror) 122 achieve focusing, with the components described and shown herein.

Moreover, the optical assembly is designed to provide a continuous focus range from 1 meter to 60 meters, from the window (or cold mirror) 122. The obscuration on the back surface of the window (or cold mirror) is quite small, and the chromatic aberration introduced by the relay 124 is corrected by the catadioptric optics.

Thus, the first embodiment provides a compact optical assembly that is useful in a laser radar system because it eliminates the need for a large scanning (pointing) mirror that is moveable relative to other parts of the laser radar system. In addition, the compact optical assembly of the first embodiment has a catadioptric configuration with a concave mirror that provides most of the optical power, and allows easier achromatization between the two required wavelengths of the pointing and measurement beams. The concave minor folds the optical path onto itself, reducing the overall size substantially. The size of the system should be small enough to allow the camera 140 (FIGS. 2, 3A) to be located on the moving part of the laser radar system, eliminating parallax effects by use of a reflective window or cold mirror that allows the camera optical axis to be collinear with the axis of the measurement beam. Since the window (or cold minor) 122 is the last optical element before the light is projected to the target, this new optical assembly allows a wide field-of-view camera 140 to be used that can point in the same direction and along the same axis as the laser radar by configuring the camera's view to be reflected off of the window (or cold mirror) 122. The obscuration is small and won't cause significant increases in the size of the spot produced at the target during laser radar operation.

Accordingly, as seen from the foregoing description, the present embodiments provides a compact optical assembly for a laser radar system, comprising catadioptric optics that moves as a unit with the laser radar system and transmits pointing and measurement beams to the outlet of the laser radar system, while eliminating the need for a scanning (pointing) mirror that is moveable relative to other components of the laser radar system. With the foregoing description in mind, the manner in which the optical assembly of the present embodiments can be implemented in various types of laser radar systems will be apparent to those in the art.
Second Embodiment The second embodiment of the present invention would have a laser radar system 100 that is configured and operates in accordance with the general principles described above in connection with FIGS. 1 and 2. Certain basic features of an optical assembly 114 according to a second embodiment of the present embodiments can be appreciated from FIGS. 7a and 7b. The optical assembly of FIG. 7a comprises a light source represented by a fiber 130 through which a pointing beam and a measurement beam are directed, a lens 132, a scanning reflector 134 and a fixed reflector that in FIG. 7a comprises a plane mirror 136. Those components co-operate to direct and focus the pointing and measurement beams from the fiber 130 along a line of sight 138 that preferably coincides with the optical axis of the optical assembly and extends through the lens 132. The fiber 130, the lens 132, the scanning reflector 134 and the plane mirror are oriented relative to each other such that the pointing and measurement beams from the fiber 130 are reflected by the scanning reflector 134 to the plane mirror 136, and reflected pointing and measurement beams from the plane mirror 136 are reflected again by the scanning reflector 134 and directed along the line of sight 138 through the lens 132. The pointing and measurement beams are then directed from the laser radar system and at the target 106.

In the embodiment of FIG. 7a, the scanning reflector 134 comprises a retroreflector that is preferably a corner cube that translates (e.g. in the z direction) relative to the fiber 130, the lens 132 and the plane mirror 136 which are all fixed to the support structure of the optical assembly. Movement (or translation) of the corner cube 134 adjusts the focus of the pointing and measurement beams along the line of sight 138 by the changing the distance the measurement beam travels between the fiber and the lens. The corner cube 134 has at least three reflective surfaces that are oriented so that (i) the pointing and measurement beams from the source are reflected through the corner cube 134 to the plane mirror 136, (ii) the pointing and measurement beams reflected from the plane mirror 136 are again reflected through the corner cube 134, and (iii) movement of the corner cube in at least one predetermined direction (e.g. the z direction in FIG. 7a) adjusts the focus of the pointing and measurement beams along the line of sight 138, in a manner that is substantially unaffected by movement of the corner cube in directions transverse to the predetermined direction or by rotations of the corner cube relative to the predetermined direction. FIG. 7b is a fragmentary, schematic illustration of the optical assembly of FIG. 7a, showing the reflection schema provided by the corner cube 134 and the plane mirror 136, that makes the reflection of the pointing and measurement beams unaffected by movement of the corner cube 134 in directions transverse to the z direction or by rotation of the corner cube relative to the z direction.

The fiber 132 is associated with a fiber beam combiner that combines a pointing beam in the visable (e.g. red) wavelength range with the measurement beam in the different, e.g. infra red (IR) wavelength range. The pointing beam and measurement beams are generated from separate sources, and are combined by the fiber beam combiner (that is located inside the base 110) in a manner well known to those in the art. The combined pointing and measurement beams are directed from the fiber 130 and focused along the line of sight 138 in the manner described herein.

Thus, with the version of the second embodiment shown in FIGS. 7a and 7b, the pointing and measurement beams are directed along the line of sight 138, and the focus of the pointing and measurement beams along the line of sight is adjusted by translation of a single element (i.e. the corner cube 134) and in a way that is insensitive to (i.e. unaffected by) movement of the corner cube in directions transverse to the z direction or by rotation of the corner cube relative to the z direction. Also, the optical assembly of FIGS. 7a and 7b is extremely compact, and made up of relatively few elements. For a given configuration, the corner cube 134 can adjust the focus of the pointing and measurement beams by translation over a distance of not more than about 22 mm relative to the fixed components (fiber, plane mirror and lens), which contributes to the compactness of the optical assembly.

With the version of the second embodiment of FIGS. 7a and 7b, the pointing and measurement beams are directed along the line of sight and to the outlet 120 of the laser radar system. The pointing and measurement beams direct the measurement beam from the laser radar system and to a spot on the target 106, where the radiation is reflected and/or scattered by the target. In accordance with the principles of a laser radar system, the optical assembly 114 will receive at least some radiation that is reflected or scattered from the target 106, and that radiation will be directed back through the fiber 130, in a manner that will be apparent to those in the art.

The size of the imaged spot of the measurement beam on the target 106 determines how much light can be collected by the optical assembly. If more light is focused onto the target, more light is reflected or scattered by the target and an appropriate fraction of that reflected or scattered light is collected by the optical assembly and focused back to the fiber 130, allowing an accurate measurement of the distance between the laser radar and the target. In other words, a smaller spot allows more measurement light to return to the optical assembly and a more accurate distance measurement to be made, using the techniques described by U.S. Pat. Nos. 4,733,609, 4,824,251, 4,830,486, 4,969,736, 5,114,226, 7,139,446, 7,925,134, and Japanese Patent #2,664,399, which are incorporated by reference herein.

In the optical assembly of the version of the second embodiment shown in FIGS. 7a and 7b, the provision of the plane mirror 136 which is fixed in relation to the corner cube 134 sends the first pass beam that leaves the corner cube back through the corner cube, while the system remains insensitive to tip/tilt of the translating corner cube relative to the z direction. The lateral translation of the corner cube 134 in the z direction still causes a shift on the first pass, but the plane mirror 136 reverses the beam back through the corner cube, where it picks up an equal and opposite shift, cancelling it out. On each pass through the corner cube, the retroreflective properties of the corner cube insure that the output beam is parallel to the input beam, regardless of the orientation of the corner cube, i.e. tip, tilt or roll. Thus, the system in FIG. 7a is therefore nominally insensitive to tip/tilt and x/y motions of the corner cube. FIG. 7b shows how the fixed plane mirror 136 makes the system insensitive to x/y, motions of the corner cube.

In addition, since the laser radar system uses two wavelengths, and the system is sensitive to backreflections, the corner cube 134 could also be a set of three mirrors (an air-corner cube), rather than a solid glass traditional corner cube Then, each beam is incident on a first surface mirror. Therefore, there are no surfaces that can create a ghost image that can contribute the noise floor for the distance measuring component of the laser radar, other than the 2" lens for providing the optical power.

Since the corner cube 134 is traversed by the beam twice and is reflected, the optical path between the fiber 130, and the lens 132 is four times the motion of the corner cube; a 1 mm motion of the corner cube changes the distance between the fiber and lens by 4 mm. Based on the known NA of the fiber of about 0.1, it can be seen that the ideal focal length for the fixed lens 132 is about 250 mm, based on an output aperture of 50 mm. Based on the Newtonian equations for object/image relationships, the total focus range required is about 88 mm between the near (1 meter) and far (60 meter) focus positions. This translates to a corner cube translation of 88/4=~22 mm Therefore, the only lens required is the 2" diameter objective lens 132.

The other big advantage of this optical assembly is that because the optical path 138 is folded through the corner cube 134 twice, the 250 mm to (88+250)=338 mm is fit into a very compact volume. The long focal length means the aberration requirements on the lens 132 are also relaxed relative to a shorter, unfolded system.

A major difference between this system and the systems where a transmissive optic(s) is (are) translated is that since the fiber is the z position reference, motion of the focusing element (the corner cube 134) changes the z position between the fiber 130 and the last lens element. Therefore, the system must know the position of the corner cube accurately enough to make a simple correction for this motion. A current system parameter has an axial position measurement accuracy of 5 μm+1.25 ppm/meter, or a minimum of 6.25 μm at 1 meter focus. This means the stage position must be measured to 6.25/4=1.56 μm, worst case. At far focus (60 m), the stage must only be known to 80/4=20 μm. Given all the advantages of this system, this seems to be a small tradeoff.

With the system of FIG. 7a, the input fiber 130 is right in the middle of the diverging output beam. If the system was built like FIG. 7a, the structure for holding the fiber 130 would block light, and some of the light would be incident directly back on the fiber, potentially introducing a noise floor. The alternative system shown in FIGS. 8a, 8b and 8c provides a way of addressing this issue.

The optical assembly 114a that is shown in FIGS. 8a, 8b and 8c provides a second version of the second embodiment, and includes a fiber 130a that provides a source of the pointing and measurement beams, a lens 132a, a scanning reflector 134a and a fixed reflector 136a. The scanning reflector 134a comprises a reflective roof that provides two reflections of the pointing and measurement beams, and the fixed reflector 136a comprises a reflective roof that also provides two reflections of the pointing and measurement beams. Also, the nodal lines 140, 142 of the reflective roofs 134a and 136a, respectively, are in a predetermined orientation relative to each other.

The version of the present invention shown in FIGS. 8a, 8b and 8c, functions in a manner that is generally similar to that of the version of FIGS. 7a and 7b. The reflective roof 134a has a pair of reflective surfaces that are oriented so that (i) the pointing and measurement beams from the source are reflected through the reflective roof 134a to the fixed reflective roof 136a, and the pointing and measurement beams reflected from the fixed reflective roof 136a are again reflected through the reflective roof 134a, and (ii) movement of the reflective roof 134a in at least one predetermined direction (e.g. the z direction in FIG. 8a) adjusts the focus of the pointing and measurement beams along the line of sight 138a FIG. 8c is a fragmentary, schematic illustration of the optical assembly of FIGS. 8a and 8b, showing the reflection schema provided by the reflective roof 134a and the fixed reflective roof 136a. Thus, the pointing and measurement beams are directed along the line of sight 138a, and the focus of the pointing and measurement beams along the line of sight is adjusted by translation of a single element (the reflective roof 134a) in the z direction relative to the fixed reflective roof 136a, the lens 132a, and the fiber 130a. The optical assembly of FIGS. 8a, 8b and 8c is extremely compact, and made up of relatively few elements. As with the previous version, the reflective roof 134a can adjust the focus of the pointing and measurement beams by translation over a distance of not more than 22 mm relative to the fixed components (fiber 130a, fixed reflective roof 136a and lens 132a), which contributes to the compactness of the optical assembly 114a.

The optical assembly of FIGS. 8a, 8b and 8c addresses the issue of the input fiber being right in the middle of the diverging output beam, so that the structure for holding the fiber would block light, and some of the light would be incident directly back on the fiber, causing a large noise floor. Specifically, instead of translating a corner cube and using a fixed mirror, the optical assembly is broken into the two reflective roofs 134a, 136a. The reflective roof 134a translates in place of the corner cube, and reflective roof 136a is fixed and rotated 90° about the optical axis relative to the translating reflective roof 134a. This optical assembly achieves the same advantages as the system in FIG. 7a with one major additional advantage and one disadvantage. The pointing and measurement beams from the input fiber 130 go to the moving reflective roof 134a, and are translated down by reflective roof 134*a*. The pointing and measurement beams then go to the fixed reflective roof 136*a*, which shifts those beams into the page. Then the beams go back through reflective roof 134*a* and come out expanded but parallel to the input fiber 130*a*. However, thanks to the fixed roof 136*a*, the beams are translated relative to the fiber 130 in the −y direction of FIGS. 8*a* and 8*b*. Therefore, there is no obscuration or backreflection issue. The disadvantage, however, is that if the translating roof rotates about the z-axis, these ideal characteristics no longer hold exactly true.

If reflective roof 134*a* rotates about y while translating, it acts like a roof and doesn't change the angle. If it rotates about x, then reflective roof 134*a* acts like a plane mirror but fixed reflective roof 136*a* removes this angle change because fixed reflective roof 136*a* is rotated about the z-axis by 90 degrees. If reflective roof 134*a* shifts in x, it does shift the beam, but then fixed reflective roof 136*a* acts like a mirror (as in the system of FIG. 7*a*) and the second pass through reflective roof 134*a* corrects the shift. Finally, if reflective roof 134*a* shifts in y, it is like a plane mirror, so there is no change for the beam.

A series of first surface mirrors (in the form of two roof prisms forming the reflective roofs 134*a*, 136*a*) is used to change the axial distance between the fiber 130*a* and the fixed lens 132*a*. This system is nominally insensitive to tip/tilt and x/y shift of the moving element (the reflective roof 134*a*). The output beam from the two roof system is shifted relative to the input fiber 130*a*, so there is no obscuration or back reflection issue. In addition, since all the surfaces are first surface mirrors, there are no interfaces that can create ghost reflections. The folded nature of the beam path makes it very compact, allowing for stable mechanics. The long focal length of the system means the fixed reflective roof 136*a* can likely be an off-the-shelf color corrected doublet.

FIGS. 9-13 schematically illustrate various concepts for configuring and orienting the components of the optical assembly of the second embodiment.

Figure 9:
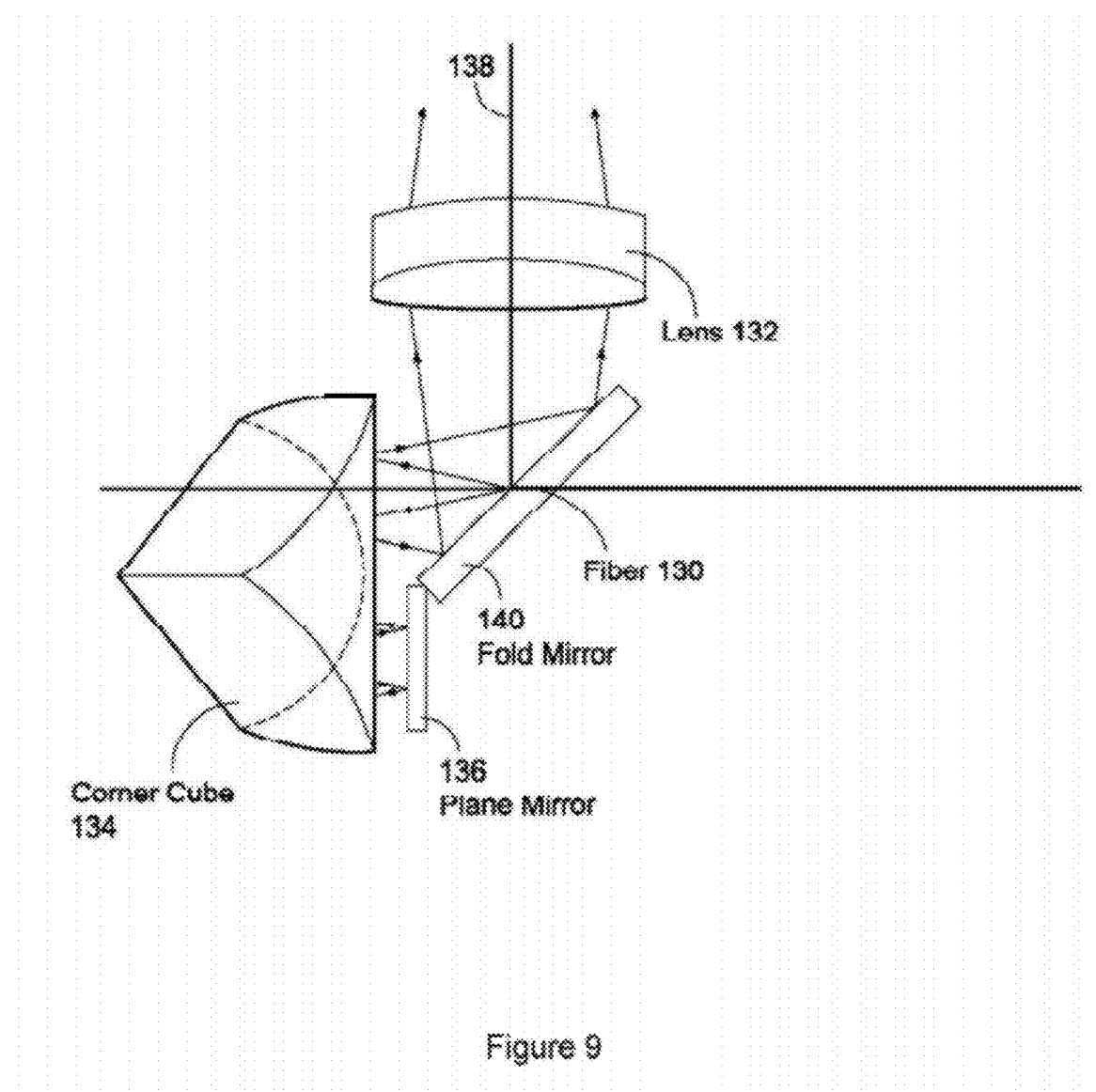
FIGS. 9-13 are schematic illustration of additional concepts of an optical assembly according to second embodiment.

For example, as shown in FIG. 9, the pointing and measurement beams reflected by the scanning reflector 134 and directed along the line of sight 138 through the lens, are reflected by a fold mirror 144 that folds the line of sight 138 of the pointing and measurement beams directed through the lens 132. As further shown in FIG. 9, the fiber 130 can be located in the fold mirror 144. The optical assembly of the present invention is designed to be focused at a range of a meter to 60 meters from the lens 132. When the system shown in FIG. 9 is focused at 1 meter from the lens, less light is directed to the target, but the light loss is only a few percent. When the optical assembly is focused at 60 meters, by movement of the corner cube 134 about 22 mm, the beam pretty much fills the aperture of the lens 132, so substantially all the light is used to make the spot that impinges on the target.

Figure 10:
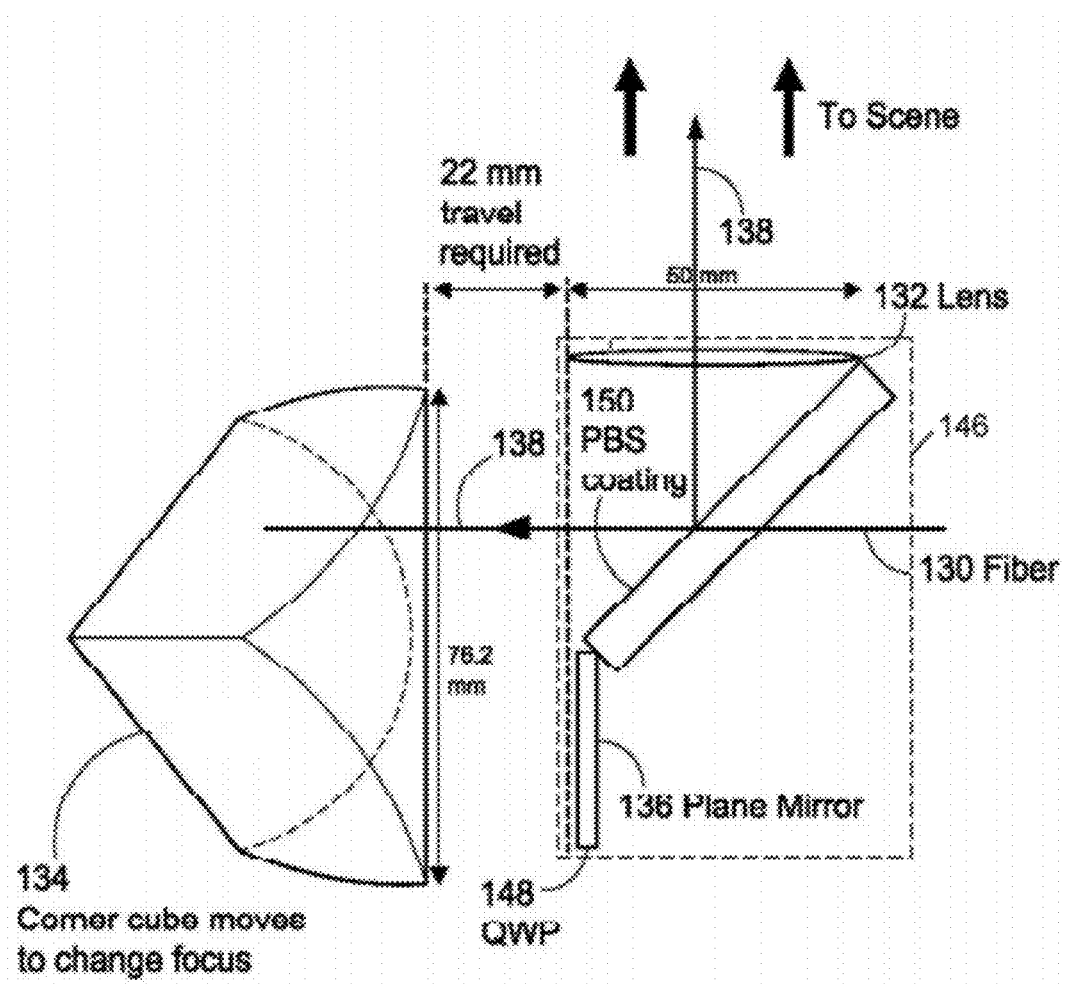

In addition, as schematically shown in FIG. 10, the lens 132, the beam source (i.e. fiber 130) and the plane mirror 136 are supported in a manner such that they can move as a unit relative to the retroreflector 134, and wherein the line of sight moves with the unit. Thus, as illustrated by FIG. 10, the lens 132, the plane mirror and the fiber 130 are supported by a box 146, so that all of those components can move as a unit relative to the retroreflector 134. Therefore, reference to the retroreflector and the other components (fiber, lens, fixed reflector) being moveable "relative" to each other can mean that the other components are fixed by a support structure, and the retroreflector moves relative to the support structure, or the support structure for the other components (e.g. the box 146 in FIG. 6) enables those other components to move (e.g. rotate) as a unit relative to the retroreflector 134.

Moreover, as also shown in FIG. 10, the pointing and measurement beams reflected by the scanning reflector 134 and directed along the line of sight through the lens 132 are reflected by a polarization beam splitter plate 150 that folds the line of sight 138 of the pointing and measurement beams directed through the lens (in a manner similar to that shown in FIG. 9). In FIG. 10, the polarization beam splitter plate 150 has a polarization beam splitting coating that enables the polarization beam splitter plate 150 to function as a polarization beam splitter, and a quarter wave plate 148 is provided on the plane mirror 136, to adjust the polarization of the beams reflected from the plane mirror 136. In FIG. 6, the optical fiber 130 that is the beam source is represented by a dot in a predetermined location relative to the polarization beam splitter plate 150.

Thus, in the concept shown in FIG. 10, the polarization beamsplitter plate (PBS) 150 is used to prevent the light being directed along the line of sight from coupling back into the fiber 130. Since the measurement beam is linearly polarized, its polarization state can be rotated 90 degrees by going through the quarter wave plate (QWP) 148 oriented at 45 degrees twice. In this case, the QWP 148 also has the second surface mirror 136 that acts as the mirror 136 of the system in the manner shown and described in connection with FIG. 7*a*. The fiber 130 is placed near the back surface of the PBS plate 150. Since it is a PBS plate and the input surface is tilted at 45 degrees relative to the fiber, any reflection off the back surface will not go back to the fiber. The corner cube 134 is solid glass, since this is an off-the-shelf part and since this increases the axial distance (physical distance) between the fiber and the lens. There is no obscuration in this optical assembly.

Also, in the concept shown in FIG. 10, the corner cube 134 can be held fixed and the plane mirror, fold mirror, lens and fiber (all of which are supported in the box 146) all rotate about the centerline of the corner cube. The rotation must be about the centerline of the corner cube or else the beams will move outside the edges of the corner cube during rotation. This concept of the second embodiment, can reduce the rotating mass that needs to be moved about an elevation axis, which would allow a smaller, lighter elevation axis motor to be used and would also result in less heat generation (the heat source being the actuator used to move the components). Also, it may result in an even more compact assembly. It can also lead to a reduction in focus stage complexity, and result in fewer cables that need to pass through a rotating joint so cable routing is simpler and cable disturbances caused by moving cables can be reduced to improve motion accuracy and thus instrument performance. Thus, this aspect of the concept of FIG. 10 can produce a smaller, simpler and more cost effective optical assembly, and reduction of cable disturbances should also improve accuracy.

Figure 11:
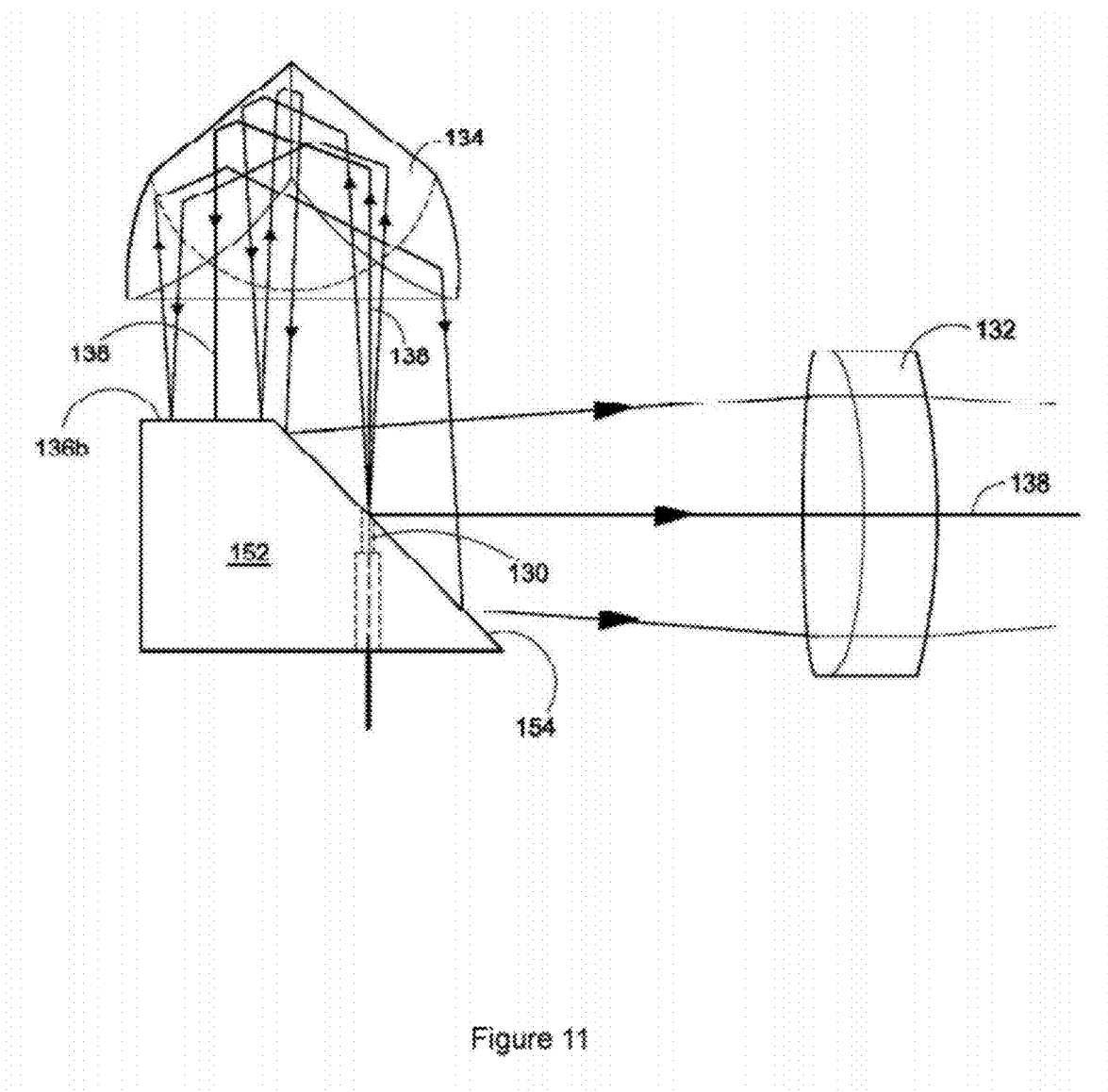

Still further, as shown schematically in FIG. 11, the source comprises an optical fiber 130 supported by a monolithic member 152 that has a portion 136*b* that functions as the plane mirror and another portion 154 that folds the line of sight 138 of the pointing and measurement beams reflected by the scanning reflector 134 and directed along the line of sight through the lens 132.

Figure 12:
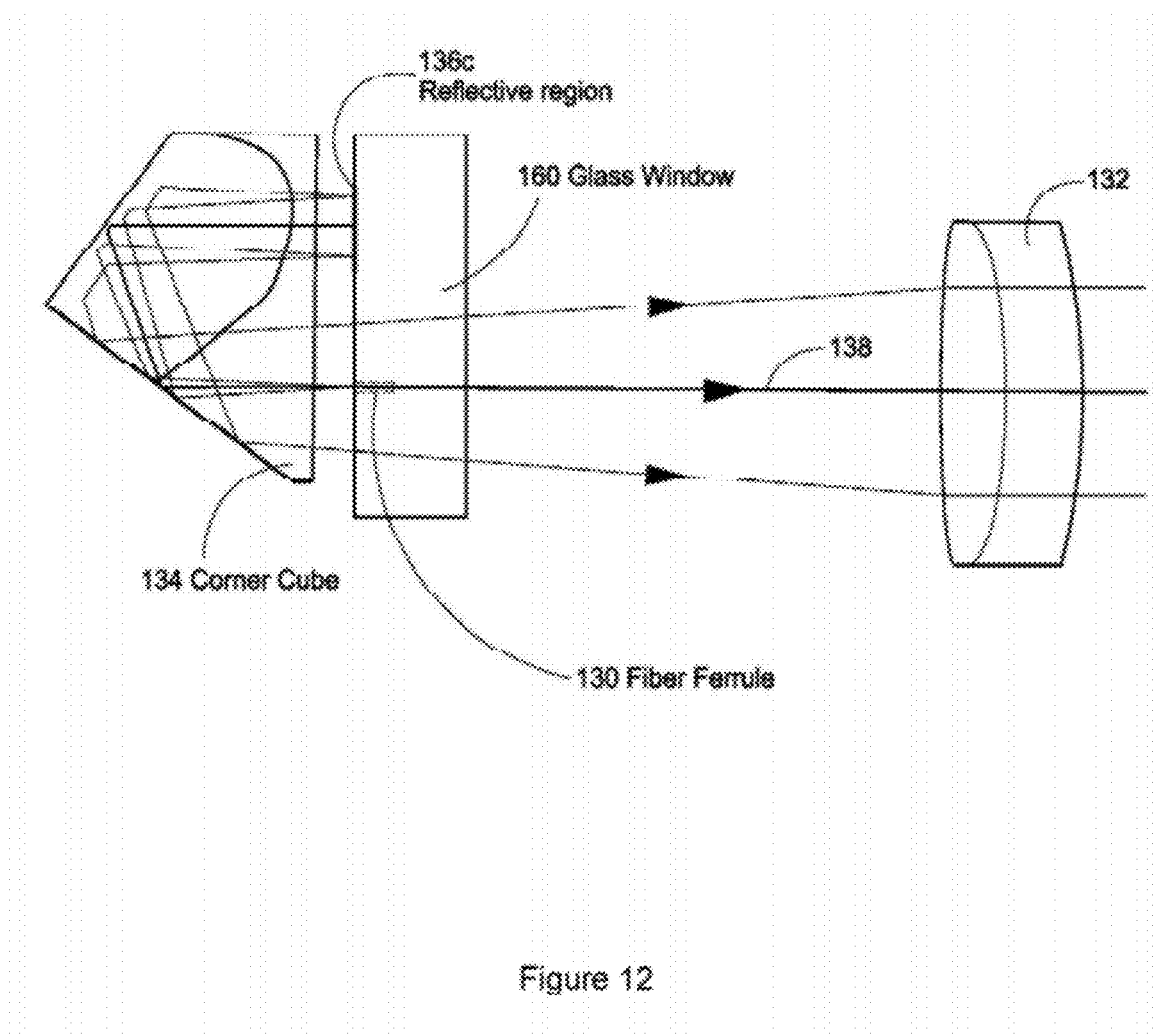

Also, as shown schematically in FIG. 12, the source can comprise an optical fiber 130 supported by a transmissive member (e.g. a glass window 160) that has a reflective portion 136*c* thereon that forms the plane mirror. In addition, the optical fiber can be supported by a mechanical structure 162 that applicants refer to as a "spider", shown in FIG. 13, that includes a series of struts 164 with a central opening 166 that forms the support for the optical fiber. The spider 162 can be made of a lightweight metal such as aluminum. Thus, the optical assembly can comprise the glass plate 160 with a hole for the fiber and a silvered area as the mirror 136c (as shown in FIG. 12) or a metal plate with the spider (FIG. 13) to hold the fiber and let light through and a separate mirror surface machined and polished that is attached to the spider, and forms the reflective portion 136c. Therefore, FIGS. 12 and 13 are similar, except that in FIG. 12 the transmissive member 160 that supports the fiber is a piece of glass, and in FIG. 13 the transmissive member is the air space(s) between the mechanical components of the spider 162.

Figure 13:
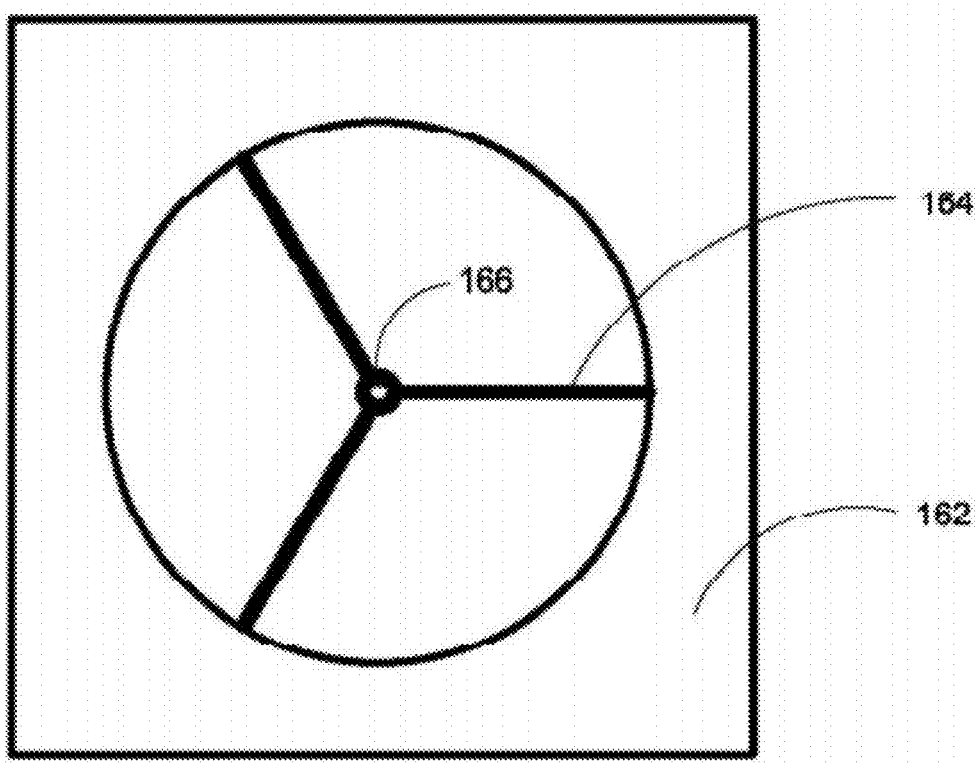

The concepts shown in FIGS. 11, 12 and 13 provide additional advantageous features to an optical assembly according to the second embodiment of the present invention. For example, the concept of FIG. 11 uses a single substrate for both mirrors and for holding the fiber. This may provide simpler fabrication, and may allow the single substrate to be formed of relatively light weight aluminum. With respect to the concepts of FIGS. 12 and 13, replacing a fold mirror with the window or window/spider arrangement, can reduce the overall weight of the optical assembly, because it eliminates the weight of a fold mirror. Also, the concepts of FIGS. 12 and 13 can reduce the requirement for additional tolerances on surface figure and mirror angle position. The result is that the corner cube now moves parallel to the optical axis of the lens rather than perpendicular to it. Thus, the optical assembly is simplified because it has one less mirror, so the angle between the mirrors is one less specification to meet. Moreover, the angle between the fiber hole and the mirror surface is more directly controllable when cutting normal to the surface (not really a problem if we use the monolithic metal mirror concept of FIG. 11). Also, the position of the fiber axis relative to the lens can be maintained more easily during fabrication (e.g. by holding both elements in a tube), thereby reducing the out-of-focus (repeatable) boresight error that occurs because the beam is not centered in the aperture. Still further because the fiber hole is parallel to the optical axis of the lens, it should also be easier to align the two, and strongly reduce thermal boresight error. Additionally, the corner cube can be closer to the fiber, so it can be smaller.

Accordingly, as seen from the foregoing description, the second embodiment of the present invention provides a compact optical assembly for a laser radar system, comprising a light source, a lens, a scanning reflector and a fixed reflector that co-operate to focus a beam from the light source along a line of sight that extends through the lens, where the light source, the lens, the scanning reflector and the fixed reflector are oriented relative to each other such that (i) a beam from the light source is reflected by the scanning reflector to the fixed reflector, (ii) reflected light from the fixed reflector is reflected again by the scanning reflector and directed along the line of sight through the lens, and (iii) the scanning reflector is moveable relative to the source, the lens and the fixed reflector, to adjust the focus of the beam along the line of sight.

In this embodiment, The laser radar system 100 has the pointing beam and measurement beam. However the laser radar system 100 may have the measurement beam without the pointing beam. For example, the measurement beam is in the visible. Therefore, in this case, the measurement beam can also play pointing beam. The laser radar system 100 of this embodiment has the different wavelength region between the pointing beam and measurement beam. However the laser radar system 100 may have the same wavelength region such as the visible region.

In an optional embodiment, the optical assembly has a lens 132, a scanning reflector 134 and a fixed reflector. However the optical assembly may have a lens 132, a scanning reflector 134 without a fixed reflector. For example, the measurement beam can be directly directed from reflector 134 to lens 132.

As for the laser radar system 100, the second embodiment is also applicable to the distance measurement system that determine six degrees of freedom ($\alpha$, $\beta$, d, $\phi$, $\chi$, $\psi$) of a reflector or of an object on which the reflector is arranged, comprises an angle-and distance measurement apparatus, e.g. a laser tracker as disclosed in US published application US2006-0222314 (which is incorporated by reference herein). As for the laser radar system 100, the present invention is also applicable to the distance measurement system that determine an distance between the measurement system and the target point and/or a change of this distance by comparison of the emitted and reflected laser light, e.g. a laser tracker as disclosed in US published application US 2011-0181872 (which is also incorporated by reference herein).

Next, explanations will be made with respect to a structure manufacturing system provided with the measuring apparatus (laser radar system 100) described hereinabove.

Figure 14:
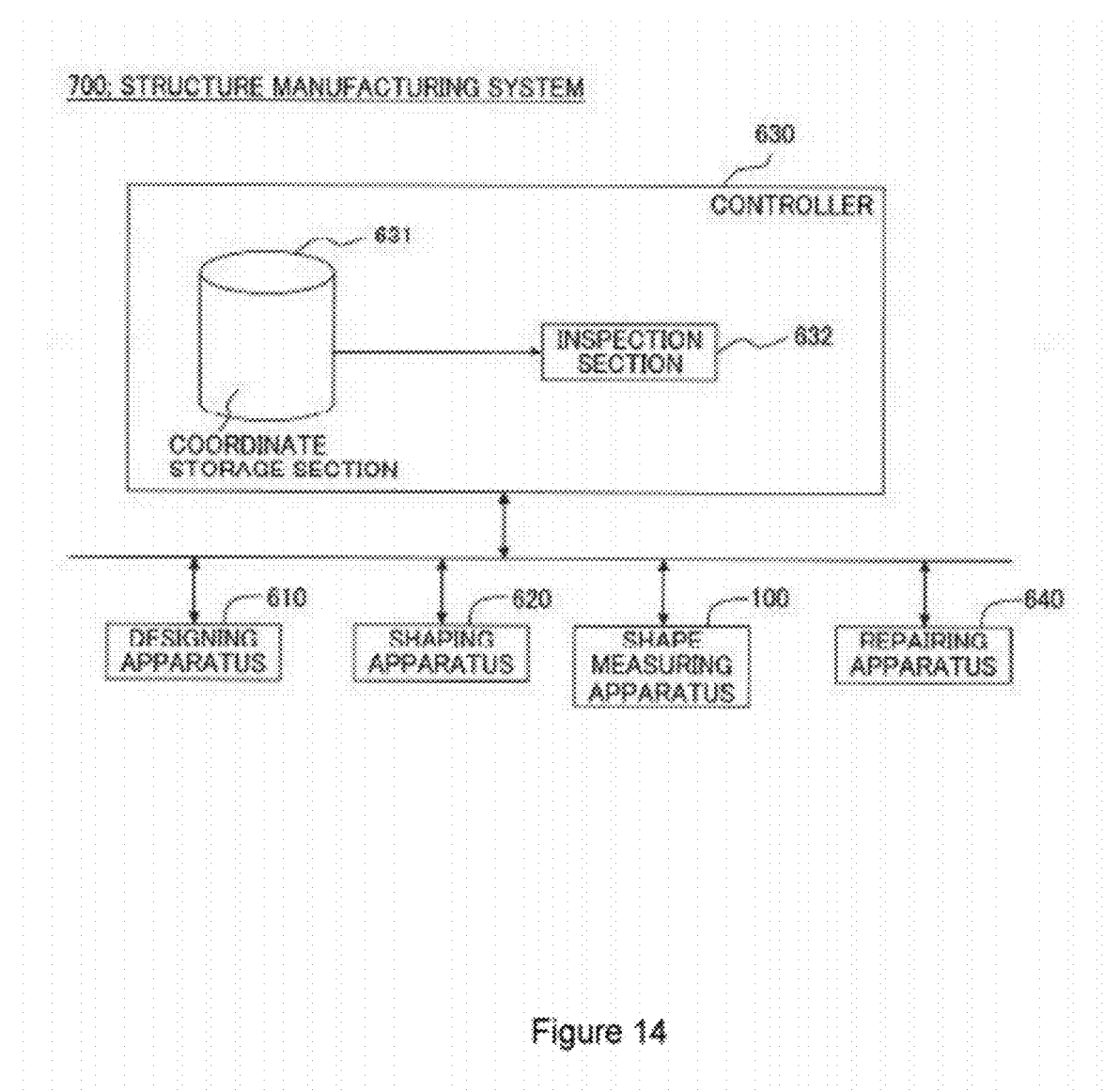
FIG. 14 is a block diagram of a structure manufacturing system 700.

FIG. 14 is a block diagram of a structure manufacturing system 700. The structure manufacturing system is for producing at least a structure from at least one material such as a ship, airplane and so on, and inspecting the structure by the profile measuring apparatus 100. The structure manufacturing system 700 of the embodiment includes the profile measuring apparatus 100 as described hereinabove in the embodiment, a designing apparatus 610, a shaping apparatus 620, a controller 630 (inspection apparatus), and a repairing apparatus 640. The controller 630 includes a coordinate storage section 631 and an inspection section 632.

The designing apparatus 610 creates design information with respect to the shape of a structure and sends the created design information to the shaping apparatus 620. Further, the designing apparatus 610 causes the coordinate storage section 631 of the controller 630 to store the created design information. The design information includes information indicating the coordinates of each position of the structure.

The shaping apparatus 620 produces the structure based on the design information inputted from the designing apparatus 610. The shaping process by the shaping apparatus 620 includes such as casting, forging, cutting, and the like. The profile measuring apparatus 100 measures the coordinates of the produced structure (measuring object) and sends the information indicating the measured coordinates (shape information) to the controller 630.

The coordinate storage section 631 of the controller 630 stores the design information. The inspection section 632 of the controller 630 reads out the design information from the coordinate storage section 631. The inspection section 632 compares the information indicating the coordinates (shape information) received from the profile measuring apparatus 100 with the design information read out from the coordinate storage section 631. Based on the comparison result, the inspection section 632 determines whether or not the structure is shaped in accordance with the design information. In other words, the inspection section 632 determines whether or not the produced structure is nondefective. When the structure is not shaped in accordance with the design information, then the inspection section 632 determines whether or not the structure is repairable. If repairable, then the inspection section 632 calculates the defective portions and repairing amount based on the comparison result, and sends the information indicating the defective portions and the information indicating the repairing amount to the repairing apparatus 640.

The repairing apparatus 640 performs processing of the defective portions of the structure based on the information indicating the defective portions and the information indicating the repairing amount received from the controller 630.

Figure 15:
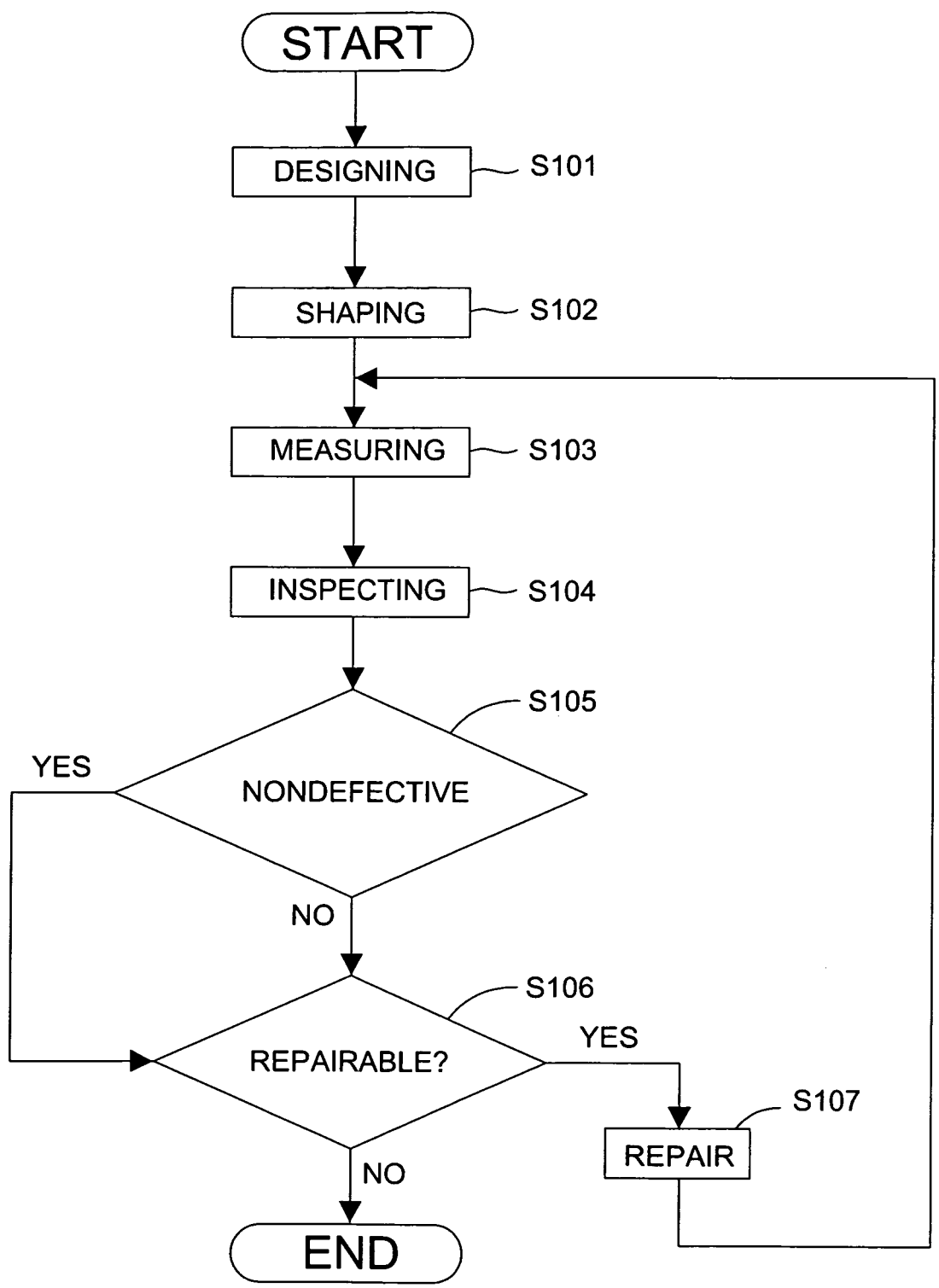
FIG. 15 is a flowchart showing a processing flow of the structure manufacturing system 700.

FIG. 15 is a flowchart showing a processing flow of the structure manufacturing system 700. With respect to the structure manufacturing system 700, first, the designing apparatus 610 creates design information with respect to the shape of a structure (step S101). Next, the shaping apparatus 620 produces the structure based on the design information (step S102). Then, the profile measuring apparatus 100 measures the produced structure to obtain the shape information thereof (step S103). Then, the inspection section 632 of the controller 630 inspects whether or not the structure is produced truly in accordance with the design information by comparing the shape information obtained from the profile measuring apparatus 100 with the design information (step S104).

Then, the inspection portion 632 of the controller 630 determines whether or not the produced structure is nondefective (step S105). When the inspection section 632 has determined the produced structure to be nondefective ("YES" at step S105), then the structure manufacturing system 700 ends the process. On the other hand, when the inspection section 632 has determined the produced structure to be defective ("NO" at step S105), then it determines whether or not the produced structure is repairable (step S106).

When the inspection portion 632 has determined the produced structure to be repairable ("YES" at step S106), then the repair apparatus 640 carries out a reprocessing process on the structure (step S107), and the structure manufacturing system 700 returns the process to step S103. When the inspection portion 632 has determined the produced structure to be unrepairable ("NO" at step S106), then the structure manufacturing system 700 ends the process. With that, the structure manufacturing system 700 finishes the whole process shown by the flowchart of FIG. 15.

With respect to the structure manufacturing system 700 of the embodiment, because the profile measuring apparatus 100 in the embodiment can correctly measure the coordinates of the structure, it is possible to determine whether or not the produced structure is nondefective. Further, when the structure is defective, the structure manufacturing system 700 can carry out a reprocessing process on the structure to repair the same.

Further, the repairing process carried out by the repairing apparatus 640 in the embodiment may be replaced such as to let the shaping apparatus 620 carry out the shaping process over again. In such a case, when the inspection section 632 of the controller 630 has determined the structure to be repairable, then the shaping apparatus 620 carries out the shaping process (forging, cutting, and the like) over again. In particular for example, the shaping apparatus 620 carries out a cutting process on the portions of the structure which should have undergone cutting but have not. By virtue of this, it becomes possible for the structure manufacturing system 700 to produce the structure correctly.

In the above embodiment, the structure manufacturing system 700 includes the profile measuring apparatus 100, the designing apparatus 610, the shaping apparatus 620, the controller 630 (inspection apparatus), and the repairing apparatus 640. However, present teaching is not limited to this configuration. For example, a structure manufacturing system in accordance with the present teaching may include at least the shaping apparatus and the profile measuring apparatus.

Thus, the present invention provides new and useful concepts for an apparatus, optical assembly, method for inspection or measurement of an object and method for manufacturing a structure. With the foregoing description in mind, the manner in which those concepts (e.g. the optical assembly of the present embodiments) can be implemented in various types of laser radar systems, as well as other types of optical systems and methods, will be apparent to those in the art.

The invention claimed is:

1. A distance measurement apparatus for measuring distance to an object, comprising:
    an optical assembly including a fixed reflector and a condenser lens configured to focus a measurement beam onto the object;
    a light source including an optical fiber supported by a support, the optical fiber being located in an optical path of a measurement beam at a position between the fixed reflector and an outlet of the optical assembly, an end of the optical fiber situated to deliver the measurement beam being located at a position along an optical axis of the condenser lens;
    a detector configured to detect the measurement beam that is reflected by the object, the measurement beam traveling from the end of the optical fiber toward the fixed reflector, and traveling backward from the fixed reflector to the object via the outlet of the optical assembly; and
    a controller configured to measure the distance to the object based at least in part on a signal from the detector.

2. The distance measurement apparatus of claim 1, wherein the portion of the measurement beam reflected by the object and received by the optical assembly is reflected by the fixed reflector, received by the optical fiber, and detected by the detector.

3. The distance measurement apparatus of claim 2, wherein:
    the optical assembly further comprises a scanning reflector, the fixed reflector and the scanning reflector being oriented such that the measurement beam from the optical fiber is reflected by the scanning reflector to the fixed reflector, from the fixed reflector again to the scanning reflector, and from the scanning reflector to the outlet;
    the portion of the measurement beam reflected by the object and received by the optical assembly is reflected by the scanning reflector toward the fixed reflector, from the fixed reflector again to the scanning reflector, and from the scanning reflector to the optical fiber such that the received portion of the measurement beam is received by the optical fiber; and
    wherein the scanning reflector is moveable relative to the fixed reflector to adjust the focus of the measurement beam along a line of sight.

4. The distance measurement apparatus of claim 3, wherein the optical assembly further comprises a lens, and the end of the optical fiber is positioned along an optical axis of the lens.

5. The distance measurement apparatus of claim 4, wherein the end of the optical fiber is positioned between the outlet and the scanning reflector.

6. The distance measurement apparatus of claims 5, wherein the scanning reflector is a retroreflector, and the fixed reflector is a plane mirror.

7. The distance measurement apparatus of claim 6, wherein:
the optical fiber and the plane mirror are fixed relative to a support structure of the optical assembly; and
the retroreflector is moveable relative to the optical fiber and the plane mirror to vary the focus of the measurement beam along the line of sight.

8. The distance measurement apparatus of claim 7, wherein the retroreflector comprises a corner cube having at least three reflective surfaces oriented such that (i) the measurement beam from the light source is reflected through the corner cube to the plane mirror, the measurement beam reflected from the plane mirror is again reflected through the corner cube, and (ii) movement of the corner cube in at least one predetermined direction adjusts the focus of the measurement beams along the line of sight.

9. The distance measurement apparatus of claim 6, wherein:
the measurement beams reflected by the scanning reflector and directed along the line of sight is reflected by a polarization beam splitter that folds the line of sight of the measurement beam; and
the optical fiber is held in a predetermined location relative to the polarization beam splitter that folds the line of sight of the measurement beams.

10. The distance measurement apparatus of claim 6, wherein the optical fiber is supported by a monolithic member that has a portion that functions as the plane mirror and another portion that folds the line of sight of the measurement beams reflected by the scanning reflector.

11. The distance measurement apparatus of claim 6, wherein the optical fiber is supported by a transmissive member that also supports the plane mirror.

12. The distance measurement apparatus of claim 6, further comprising a member defining an opening, wherein the optical fiber is positioned in the opening, and the member includes a plurality of support members positioned around the opening.

13. The distance measurement apparatus of claim 3, wherein:
the scanning reflector comprises a reflective roof that provides two reflections of the measurement beam; and
the fixed reflector comprises a reflective roof that provides two reflections of the measurement beam, respective nodal lines of the reflective roofs being in a predetermined orientation relative to each other.

14. The distance measurement apparatus of claim 6, wherein:
the light source and the plane mirror are supported in a manner such that they can move as a unit relative to the retroreflector; and
wherein the line of sight moves with the unit.

15. The distance measurement apparatus of claim 13, wherein the measurement beam reflected by the scanning reflector and directed along the line of sight through the lens, is reflected by a fold mirror that folds the line of sight of the beam directed through the lens.

16. The distance measurement apparatus of claim 15, wherein the optical fiber is supported by the fold mirror.

17. The distance measurement apparatus of claim 2, wherein the optical assembly includes catadioptric optics.

18. The distance measurement apparatus of claim 17, wherein the optical assembly includes at least one moveable optic to vary focus of the measurement beam.

19. The distance measurement apparatus of claim 18, wherein the focus of the measurement beam is changed by moving a plurality of optics.

20. The distance measurement apparatus of claim 1, further comprising a first motor configured to rotate the optical assembly around a first axis, and a first encoder configured to monitor a position of the optical assembly rotated by the first motor.

21. The distance measurement apparatus of claim 20, wherein the optical assembly comprises a second motor configured to rotate the optical assembly around a second axis perpendicular to the first axis, and a second encoder configured to monitor a position of the optical assembly rotated by the second motor.

22. The distance measurement apparatus of claim 20, wherein a pointing beam having a wavelength different from a wavelength of the measurement beam propagates along the optical path of the measurement beam.

23. A distance measuring apparatus including the apparatus of claim 20, wherein the controller is configured to measure a distance of the object based on the signal from the detector.

24. The distance measuring apparatus of claim 23, wherein a portion of light from the light source is the measurement beam, and another portion of the light from the light source is a reference beam, and the distance measuring apparatus measures the distance of the object based at least in part on the reference beam and a portion of the measurement beam reflected from the object.

25. A method of manufacturing a structure, comprising:
producing the structure based on design information;
obtaining shape information of the structure by using the apparatus of claim 1; and
comparing the obtained shape information with the design information.

26. The method of claim 25, further comprising reprocessing the structure based on the comparison result.

27. The method of claim 25, wherein reprocessing the structure includes producing the structure over again.

* * * * *